(12) United States Patent
Ragland

(10) Patent No.: US 8,879,801 B2
(45) Date of Patent: Nov. 4, 2014

(54) IMAGE-BASED HEAD POSITION TRACKING METHOD AND SYSTEM

(75) Inventor: Richard R. Ragland, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 57 days.

(21) Appl. No.: 13/251,530

(22) Filed: Oct. 3, 2011

(65) Prior Publication Data

US 2013/0083976 A1  Apr. 4, 2013

(51) Int. Cl.
*G06K 9/00* (2006.01)
*G06F 3/01* (2006.01)

(52) U.S. Cl.
CPC ............ *G06K 9/00268* (2013.01); *G06F 3/012* (2013.01); *G06F 3/013* (2013.01); *G06K 9/00* (2013.01); *G06K 9/0061* (2013.01); *G06F 3/011* (2013.01)
USPC ........... 382/117; 382/103; 382/128; 382/129; 382/130; 382/173; 351/209; 351/210; 351/246

(58) Field of Classification Search
CPC .................. G02B 2027/0187; G02B 27/0172; G02B 27/0093; G06K 9/00221; G06K 9/00597; G06K 9/0061; G06K 9/00201; G06T 2207/30041; G06T 19/003; A61F 9/0017; A61F 2009/00872; A61B 3/0025; A61B 3/113; A61B 3/14; A61M 16/01; G02C 7/048; G06F 3/011; G06F 3/013; H04N 5/2253; H04N 5/2259; H04N 5/2628; B60R 2021/01566
USPC .......... 382/103, 117, 128, 173, 294; 351/208, 351/209, 246
See application file for complete search history.

(56) References Cited

U.S. PATENT DOCUMENTS 4,973,149 A * 11/1990 Hutchinson ................... 351/210
5,471,542 A   11/1995 Ragland
(Continued)

FOREIGN PATENT DOCUMENTS

EP     1484665 A2    12/2004
WO     2005059736 A1  6/2005
WO     2008141460 A1  11/2008

OTHER PUBLICATIONS

International Search Report and Written Opinion—PCT/US2012/000499—ISA/EPO—Apr. 4, 2013.
(Continued)

*Primary Examiner* — Vu Le
*Assistant Examiner* — Aklilu Woldermariam
(74) *Attorney, Agent, or Firm* — Jeffrey D. Jacobs

(57) ABSTRACT

Systems and methods for tracking a head position of a user include obtaining digital images of the user's head, processing the images to locate anatomical structures beneath the visible surface, and using those determined locations as inputs to a computing device. In an embodiment, images of a user's face are processed to identify the irises of the eyes, identify pixels along a boundary between each iris and the surrounding sclera, determine an ellipse defined by the identified iris-sclera boundary pixels, determine a distance-to-pixel ratio based on a pixel length of a long axis of such an ellipse compared to a known or presumed diameter of the iris, locating the iris in a three-axis coordinate system, determining an optical axis vector of the eye in the three-axis coordinate system, and calculating a center of the eyeball based on the optical axis vector and a known or presumed eyeball radius.

24 Claims, 20 Drawing Sheets

(56) References Cited

U.S. PATENT DOCUMENTS

| | | | | |
|---|---|---|---|---|
| 5,912,721 | A * | 6/1999 | Yamaguchi et al. | 351/210 |
| 6,351,573 | B1 * | 2/2002 | Schneider | 382/294 |
| 7,043,056 | B2 * | 5/2006 | Edwards et al. | 382/103 |
| 7,596,242 | B2 * | 9/2009 | Breed et al. | 382/103 |
| 8,077,914 | B1 * | 12/2011 | Kaplan | 382/103 |
| 8,433,105 | B2 * | 4/2013 | Choi et al. | 382/117 |
| 2002/0175994 | A1 * | 11/2002 | Sakakibara et al. | 348/135 |
| 2006/0110008 | A1 * | 5/2006 | Vertegaal et al. | 382/103 |
| 2007/0014451 | A1 * | 1/2007 | Dwyer et al. | 382/128 |
| 2008/0181452 | A1 | 7/2008 | Kwon et al. | |
| 2008/0192990 | A1 | 8/2008 | Kozakaya | |
| 2009/0196460 | A1 | 8/2009 | Jakobs et al. | |
| 2009/0213071 | A1 | 8/2009 | Li et al. | |
| 2009/0252382 | A1 | 10/2009 | Liu et al. | |
| 2009/0295738 | A1 | 12/2009 | Chiang | |
| 2009/0304237 | A1 * | 12/2009 | Yoshikawa et al. | 382/116 |
| 2010/0013949 | A1 | 1/2010 | Miyamoto | |
| 2010/0125816 | A1 | 5/2010 | Bezos | |
| 2011/0150334 | A1 * | 6/2011 | Du et al. | 382/173 |

OTHER PUBLICATIONS

Kim K.N., et al., "Vision-based eye-gaze tracking for human computer interface", Systems, Man, and Cybernetics, 1999, IEEE SMC '99 Conference Proceedin GS. 1999 IEEE International Conference on Tokyo, Japan Oct. 12-15, 1999, Piscataway, NJ, USA, IEEE, US, vol. 2, Oct. 12, 1999, pp. 324-329, XP010363574, DOI: 10.1109/ICSMC.1999.825279 ISBN: 978-0-7803-5731-0, p. 326.

Moore et al., "A geometric basis measurement of three-dimensional eye position using image processing", Vision Research, Pergamon Press, Oxford, GB, vol. 36, No. 3, Feb. 1, 1996, pp. 445-459, XP022259776, ISSN: 0042-6989, DOI: 10.1016/0042-6989(95)00130-1 the whole document.

Ohno T et al., "FreeGaze: a gaze tracking system for everyday gaze interaction", 38 Proceedings ETRA 2002 Eye Tracking Research & Applications Symposium. New Orleans, LA, Mar. 25-27, 2002, New York, NY: ACM, US, Mar. 25, 2002, pp. 125-132, XP002336136, DOI: 10.1145/507072.507098 ISBN: 978-1-58113-467-4.

Partial International Search Report and Written Opinion—PCT/US2012/000499—ISA/EPO—Feb. 4, 2013.

Wang J. G., et al., "Gaze determination via images of irises",. Image and Vision Computing, vol. 19, No. 12, Oct. 1, 2001, pp. 891-911, XP055057213, ISSN: 0262-8856, DOI: 10.1016/50262-8856(01)00051-8- p. 899.

Yamazoe H, et al., "Remote and head-motion-free gaze tracking for real 38 environments with automated head-eye model calibrations", Computer Vision and Pattern Recognition Workshop, 2008. CVPR Workshops 2008. IEEE Computer Society Conference On, IEEE, Picataway, NJ, USA, Jun. 23, 2008, pp. 1-6, XP031285740, ISBN: 978-1-4244-2339-2.

A. Bradley, et al. "Modeling off-axis vision—I: the Optical effects of decentering visual targets or the eye's entrance pupil"; In Peli, E. (Ed.); Vision Models for Target Detection and Resolution; Singapore: World Scientific Press; 1995.

M. Lourakis, et al. "SBA: A Software Package for Generic Sparse Bundle Adjustment"; ACM Transactions on Mathematical Software; vol. 36, No. 1; Article 2; Mar. 2009.

* cited by examiner

IMAGE-BASED HEAD POSITION TRACKING METHOD AND SYSTEM

FIELD OF THE INVENTION

This application relates in general to methods and systems for tracking movements of a human using a digital camera, and more particularly to determining location and relative motion of a human head based on anatomical features not directly visible in an image.

BACKGROUND

Computer input methods and systems that track movements of users with a digital camera are limited to analyzing visible features, such as the hands, head or eyes. However, such anatomical features vary significantly from one person to the next, and the apparent shapes of such visible anatomical features vary widely depending upon the orientation of the imaged anatomy, user expression, etc. Consequently, such visual tracking systems may exhibit significant positioning errors, both in recognizing the features to be tracked and in accurately determining their location and orientation in three-dimensional space.

SUMMARY

The various embodiments provide systems, devices, and methods for determining location and relative motion of the head of a user by determining from digital images of the face locations of features that are not visible in the image. Further, the methods and systems herein described also determine several related biometrics for a human user, including the optical axis vectors of the user's eyes, the radii of the eyeballs, the distance between the centers of the two eyeballs, the visual axis vector offsets (in relation to the optical axis vectors), the radii of the irises, and the iris grayscale (or color) contour maps across a single, invariant section through each imaged iris. The embodiments provide a reliable measure of the user's head location and motion that is unaffected by the direction in which the user's eyes may be focused. In an embodiment, the optical axis vectors for a user's eyes are used to locate the center points of the user's eyeballs. The center of the eyeball is generally invariant to the user's gaze point—whether left, right, up or down—and is otherwise generally fixed with relation to the user's head as a whole. The positions of one or both eyeball center points may therefore be tracked within a three-axis coordinate system and used to monitor a user's head motion. When tracking the positions of both eyeball center points, the distance between these two points is easily calculated. Head motion—left and right, up and down, back and forth—may be used to implement a variety of user interfaces, such as a cursor on a display screen, or to manipulate objects remotely, navigate virtual realities, etc. In a further embodiment, the radiuses of the user's eyeballs may be estimated by determining the optical axis vectors of the user's eyes when looking in a variety of directions and identifying a location where the various optical axis vectors for a particular eye intersect, and calculating the distance between the intersection point and the origin of the optical axis vector for that eye.

In a further embodiment, optical axis vectors and eyeball centers may be used to determine a user's visual axes, which define the user's instantaneous point-of-gaze. The user's point-of-gaze may serve as a user interface, or a component of a user interface. In a further embodiment, iris grayscale or color contour maps across a single, invariant section through each iris may be determined and utilized in biometric identification applications. For more accurate results, the methods described herein may be iterated to arrive at relatively accurate measures of the visual axes, iris disc diameters, optical axis vectors, and eyeball centers.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
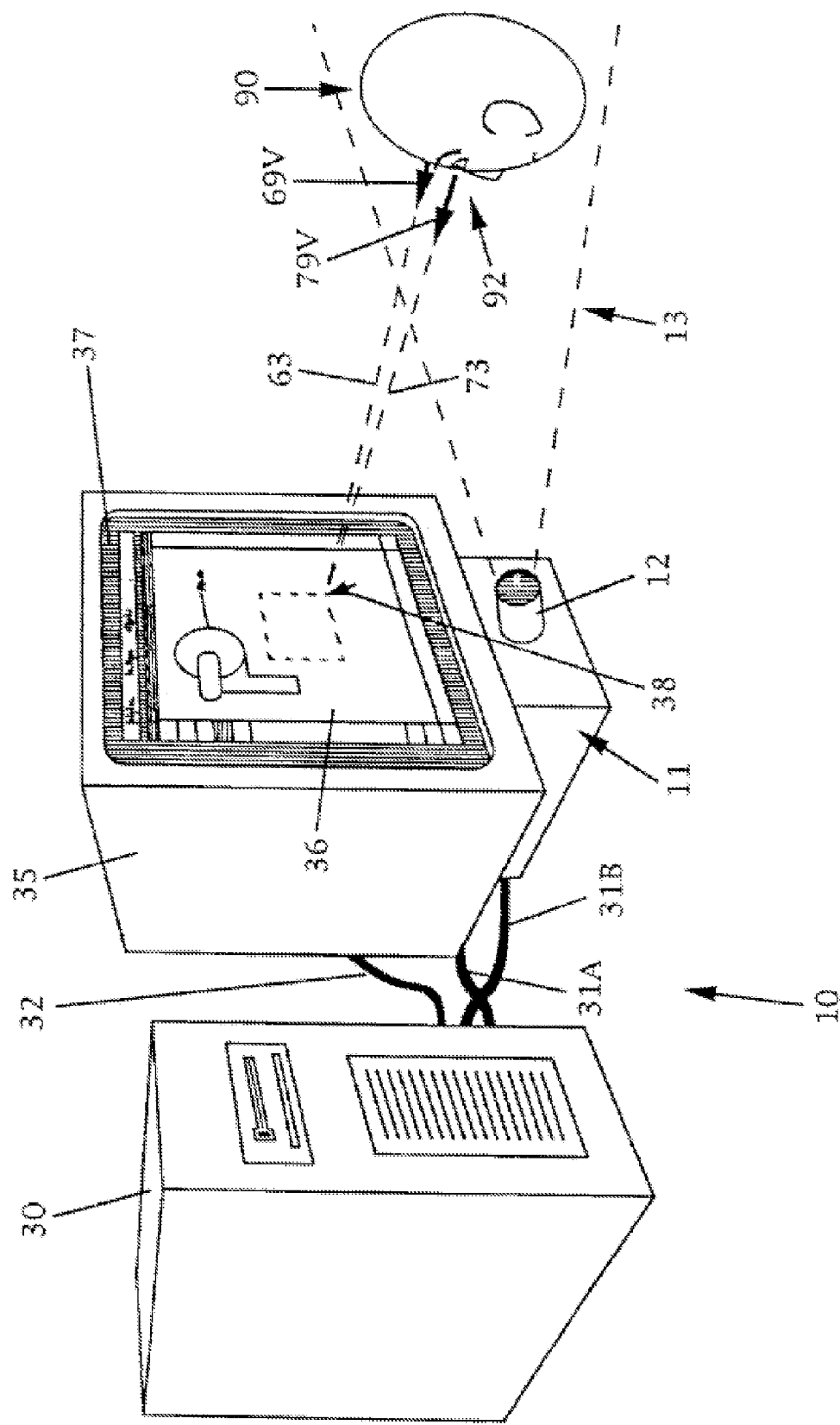
FIG. 1 is a perspective drawing of an exemplary head tracking system.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

As used herein, including in the claims, the word "ellipse" includes the special case of a circle rotated in any orientation or direction in the space within an image sensor's field of view, which nearly always presents as an ellipse (as projected into images).

As used herein, a person's point-of-gaze is the point in the surrounding space that is the instantaneous object of a user's visual regard. A point-of-gaze tracker determines a vision vector for an eye of an operator. An example of a point-of-gaze tracker is disclosed in U.S. Pat. No. 5,471,542 entitled "Point-of-gaze tracker," the entire contents of which are hereby incorporated by reference. Such a point-of-gaze tracking system enables users to provide inputs to and potentially control a computing device merely by gazing at a display. For example, U.S. Pat. No. 5,471,542 discloses a system that enables a user to control a cursor by gazing at a computer display; the cursor basically follows the user's gaze so it is always at the center of where the user is looking.

While a point-of-gaze tracker enables hands free control of computing devices, the rapid movement of a user's eyes (such as while glancing quickly about a computer screen) can result in control difficulties and user distraction. To overcome these limitations the embodiments disclosed in this application track the movement of the user's head, permitting users to control a computer system by turning their head to face a point of interest. Since the embodiment methods track head movement, the inputs to the computer system are not impacted by the user's rapid eye movements.

Other systems for tracking head movement have used recognizable facial features, in particular the eyes, to estimate the orientation of the user's head. However, such systems have suffered from errors resulting from the fact that human eyes vary in size and separation distance. Thus, without careful calibration to a user, such systems may be unreliable. Further, methods that depend on finding the center of the visible portion of the eyes in an image suffer from the problem that the iris is seen as a circular object only when the optical axes of the user's eyes are parallel to the optical axis of the camera; at all other angles of gaze the iris appears as an ellipse, which can result in errors in the estimation of head position and orientation. To overcome these limitations, the various embodiments track the movement of the user's head based upon the location of the interior center of both eyeballs. The center of each eyeball remains in a fixed location with respect to the user's skull, and thus does not change shape, location, or orientation as users shift their gaze, turn their heads or change their expressions. As a result, the various embodiments provide mechanisms for tracking the location and orientation of users' heads that are not prone to the errors that plague previously disclosed methods.

In overview, the various embodiments determine the location of the centers of a user's eyeballs by locating the user's eyes in a digital image, analyzing the digitized image to identify a plurality of points defining the iris ellipse (e.g., by analyzing the different light intensities in the image in the locations of the eyes), using the points to determine an optical axis vector for each eye, and projecting the optical axis vector into the eye by the radius of each eyeball. Having determined the location of both eyeball centers in a three-axis coordinate system, the location and orientation of the user's head is easily determined. The various embodiments make use of the iris diameter and eyeball diameter, both of which may be measured by the image processing and calculation algorithms of the various embodiments. The positions of one or both eyeball center points may therefore be tracked within a three-axis coordinate system and used to monitor head motion. Head motion—left and right, up and down, back and forth—may then be used to implement a variety of user interfaces, such as a cursor on a display screen. A system implementing the embodiment methods generally include a video or still digital camera oriented so as to observe the face of a user, and a processor that is coupled to the camera and configured with executable software instructions to perform the embodiment methods for analyzing the facial images and calculating the eyeball center locations. Such a system may be implemented on any of a variety of computing systems, including personal computers and mobile devices equipped with a suitably positioned digital camera and a processor configured with software instructions implementing the embodiment methods.

An example embodiment system is shown in FIG. 1 which is used to illustrate the various aspects. Specifically, FIG. 1 shows a perspective drawing of a personal computer system, denoted generally as 10, which includes a user-imaging camera 11. The camera 11 in this illustration is physically attached to the personal computer monitor 35 so that it can image a user's head 90. The camera 11 may include a lens assembly 12, a charge coupled device (CCD) imaging array positioned at an image plane produced by the lens 12, an image processor, a control processor, memory and camera control electronics. In the illustrated example, the computer 30 is connected by a cable 32 to the monitor 35. Based upon the size of the CCD array and magnification of the lens 12, the camera 11 will have a field-of-view 13 shown bounded by dashed lines, which in the illustrated example encompasses the user's head 90. So positioned, the camera 11 can image the user's eyes 92. In an embodiment, the position and orientation of the camera 11, and more particularly the lens 12, is physically fixed relative to the monitor 35 in order to maintain a constant geometric relationship between the camera's field-of-view 13 and the monitor screen 37 at which the user will typically be looking.

The monitor screen 37 may present to the user the output of any standard software package running on the computer 10, such as the drawing environment 36 as illustrated. In the various embodiments the user is able to make inputs to the computer 10 by moving his/her head 90 which may be interpreted by the computer 30 to control the movement and position of graphical objects, such as cursor 38 in much the same way as with a manual computer mouse (not shown).

FIG. 1 also illustrates how the user may gaze at a point on the monitor screen 37. The user's visual axes 63, 73 for the left and right eyes, respectively, are represented by dashed lines. These visual axes 63, 73 (i.e., lines of sight) are not coincident with the optical axis vectors 69V and 79V, respectively, of the user's eyeballs, but both visual axes 63, 73 do align with their respective optical axes at fixed, solid angle offsets, and these solid angles are relatively small, subtending less than 5 degrees by some studies (e.g., Modeling off-axis vision—I: the OPTICAL effects of decentering visual targets or the eye's entrance pupil, by Arthur Bradley and Larry N. Thibos, School of Optometry, Indiana University, Bloomington, Ind. 47405).

Figure 2:
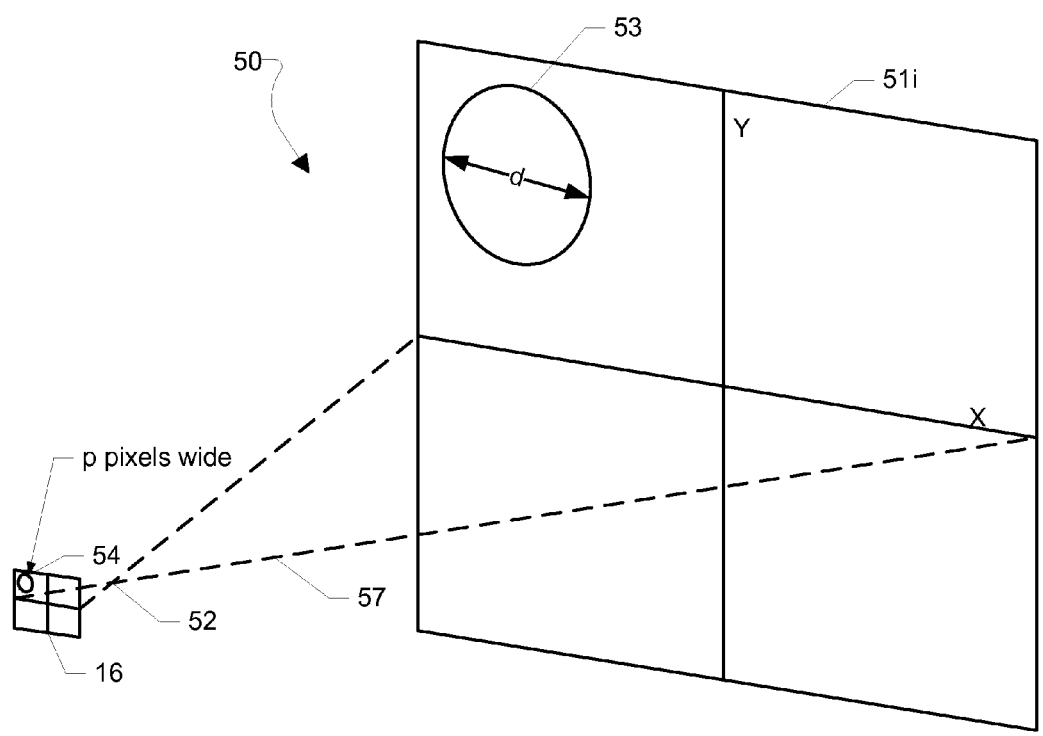
FIGS. 2 and 3 are perspective and side view diagrams, respectively, of a pinhole camera model useful for defining terms and explaining details implemented in the various embodiments.
Figure 3:
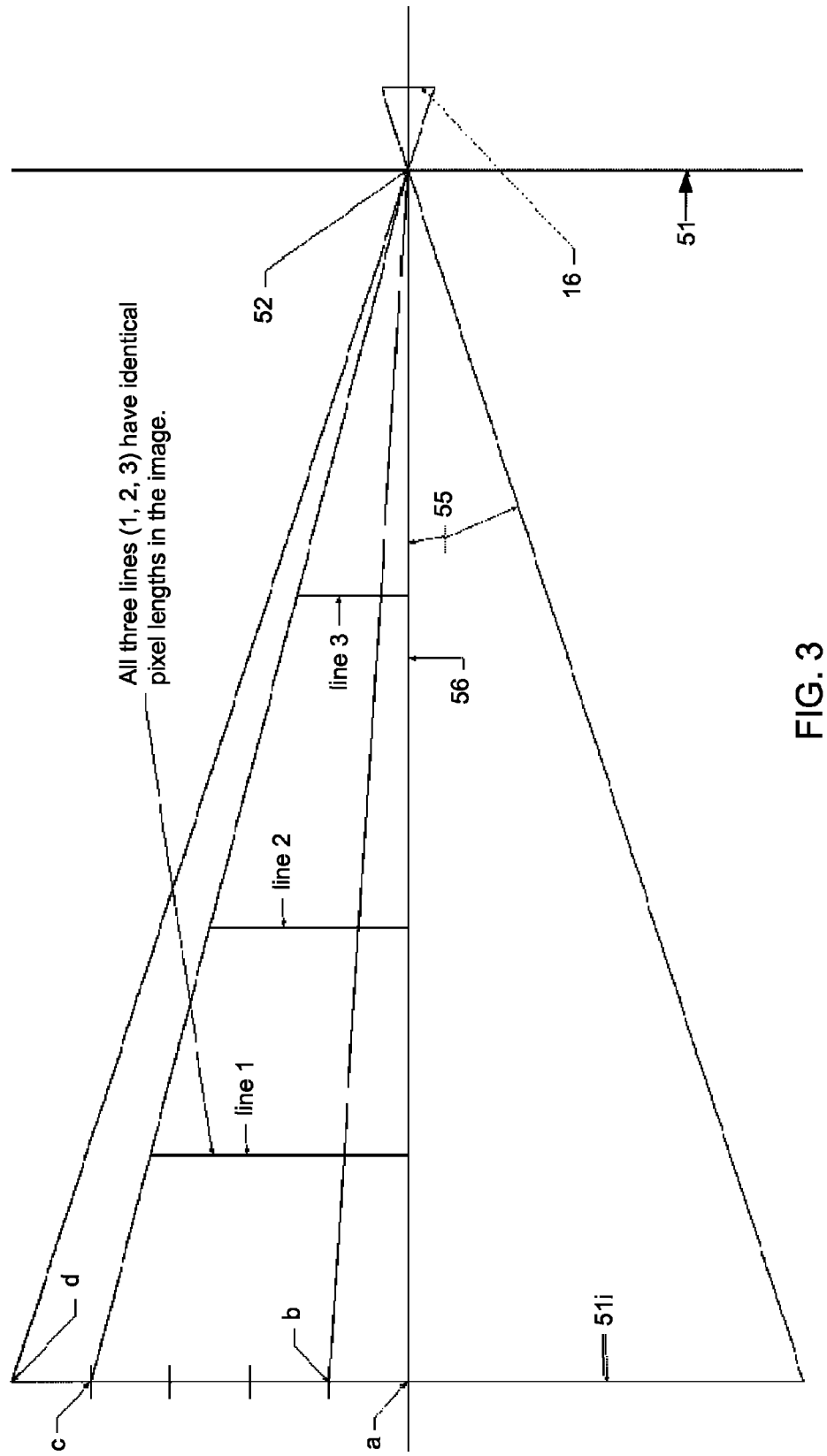

The various embodiments determine the position and relative motion of a user's head within a three-axis coordinate system that is tied to the image sensor's optics. This three-axis coordinate system is illustrated in FIGS. 2 and 3, which show some of the axes and measurements used in the various embodiments within a simple pinhole camera model. For ease of reference, the plane formed by the surface of the camera's imaging sensor (i.e., the plane onto which the camera's optics projects images within its field of view) is referred to herein as the "image sensor plane." It should be clear to those well versed in optics that the pinhole camera model features a precise linear relationship between the digital camera's sensor plane and any plane in space which is parallel to the image plane.

Referring to FIGS. 2 and 3 together, in these illustrations of a pinhole camera model, the Z-axis 56 of the three axis coordinate system passes through a plane 51$i$ which is parallel to the XY plane and the plane of the CCD, and also through the vertex 52 of the image sensor's field of view 57, and through the center point of the image sensor's CCD plane 16. The z-axis 56 is defined as coincident with the optical axis of the image sensor. The X and Y axes are perpendicular to the Z-axis 56, and the origin of all three axes (0,0,0) is defined to be coincident with the vertex 52 of the image sensor's field of view (FOV). For clarity, the XY plane may also be thought of as coincident with the "virtual" image plane upon which the methods described herein operate. In these figures, the extent of the field of view 57 is illustrated with dashed lines. The portion of the field of view angle 55 is the angle between the Z-axis 56 and the line of sight at the edge of the field of view 57, or one half of the angle spanned by the field of view 57. In FIG. 3 the upper half of 51$i$ is shown divided by tick lines, as a calibration target might be marked in order to calculate a precise field of view angle from images of the target captured at different distances from the image sensor.

Referring to FIG. 2, assuming the image sensor of camera 11 is optically distortion free, or one for which any native distortion is well compensated algorithmically, any circle (such as a conveniently located iris disc within an image of a user) that lies entirely within a parallel image plane 51$i$ in the field of view 57 will be projected into the image sensor plane 16 as a circle 54, wherever in the parallel plane it is placed. As a corollary, referring now to FIG. 3, the identical distances a-b and c-d between tick marks, must necessarily span an identical number of pixels when captured in an image, even though, as is clearly illustrated, the angle subtended by line a-b is larger than that subtended by the line c-d. Thus, this pin-hole camera model dictates that any objects entirely within a plane parallel to the plane of the image sensor's CCD 16, and within the field of view (such as those objects printed on a calibration target), must be depicted in images exactly as they are located and sized on the parallel plane, in relative terms. Thus, there is a precise linear relationship between any parallel plane and the image plane. Further, assuming line1, line2, and line3 are all in the same plane—the YZ plane, for example, or the XZ plane, or any plane rotated about the Z-axis—when captured in an image, all three lines originating on the Z-axis and extending to the ray between c and the coordinate system origin 52, must necessarily span an identical number of pixels even though, as is clearly illustrated, the three lines are of different lengths. Thus, this pin-hole camera model also dictates that any length of pixels, when measured from the center of the image, represents a distinct angle—such as the angle subtended between the z-axis and the ray intersecting the outside endpoints of lines 1, 2, and 3. Because it is necessary to compute these angles in the embodiments, a calibration target may be used to find the pixel-to-angle computation function for an image sensor at any particular focus and aperture setting. In FIG. 3, there is an obvious geometric relationship between the field of view (FOV) and the target. If the target dimensions are known, along with the FOV angle, the distance to the target from the vertex 52 (0,0,0) along the Z-axis may be easily determined. Using this same geometry, the distance from the plane of the CCD to the vertex 52 may also be easily measured in pixels (CCD pixel dimensions in mm are specified for every CCD, which may be converted to an integer, or even partial, pixel values). Using this measure of the distance from the plane of the CCD to the vertex, the pixel-to-angle transform may be computed using a simple trigonometric function. For the image sensor used in the development of this method, at example settings for both focus and aperture, the pixel-to-angle function was determined to be:

$$\phi_i = a\tan(h_i/3726.06)$$ Equation 0

Where $\phi_i$ is the spatial angle between a ray and the z-axis (such as angles $\phi_1$, $\phi_2$ & $\phi_3$ in FIG. 10), $h_i$ is the pixel length in an image from (0,0) to any point (such as the lengths $a_1$, $a_2$ & $b_1$ in FIG. 10A), and 3726.06 is the length in pixels between the vertex 52 and the plane of the CCD along the z-axis. The use of this function implies the use of a "staring" image sensor (i.e., focus and aperture are not variable) in the embodiments.

Figure 4:
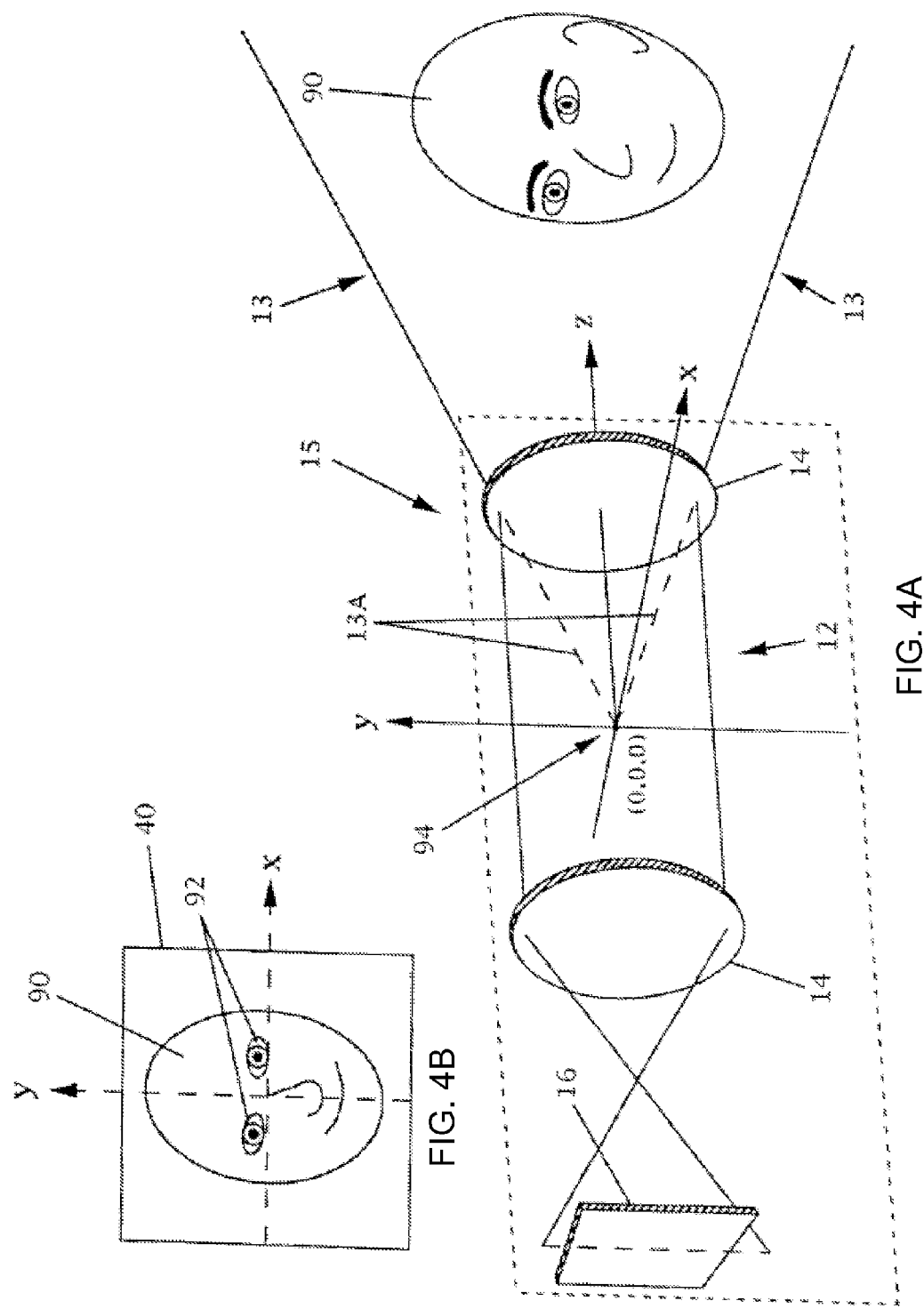
FIG. 4A is an optical system block diagram of elements of an imaging system showing spatial reference axes.
FIG. 4B is a diagram of the image plane showing the reference axes.

FIGS. 4A and 4B illustrate the physical relationships between a user 90 and the lens 12 which form a part of a digital imager 15 in an XYZ three-axis coordinate system 94 providing the physical frame of reference used in the calculations of the various embodiments. The camera's optical lenses 14 within the lens assembly 12 transmit light, bounded by the field-of-view 13, to the CCD array 16, which forms images upon which the methods described herein operate. If light rays representing the limits of the field-of-view 13 are extended inside the lens 12 (along dashed lines 13A), they will meet in a point (0,0,0), which the embodiments define as the origin of the three-axis coordinate system. As discussed above with reference to FIGS. 2 and 3, the X and Y axes of this coordinate system are parallel to the plane 16 of the image sensor's CCD, and the Z axis is orthogonal to that plane.

Images of the three-dimensional world outside the camera, as collected by the image sensor's CCD, may be treated as a projection of that world upon a virtual image plane divided by X and Y axes, which is representatively shown as plane 40 in FIG. 4B. Inside the electronics of the digital camera 11, these objects are projected onto an array of pixel sensors (e.g., CCD elements), which output signals representative of the intensity of incident light. In the electronics of the imaging sensor, the signals from the imaging sensor are output as an array of digitized pixel (picture element) color or gray-scale values which are stored in memory. The pixel values in that array may be organized by bisecting the image plane with X and Y axes as shown, with one quarter of the pixel values located in each quadrant. Further, for the purposes of describing the various embodiments, the virtual image plane may be considered to occupy a particular position in physical space; that is where the X and Y axes of the image plane exactly coincide with the X and Y axes of the XYZ three-axis coordinate system 94. Consequently, the physical relationships between all elements shown in FIG. 4A are well defined. The digital imager 15 may be physically attached to that scene which is the object of the user's visual regard (e.g., the computer's monitor screen 37 in FIG. 1). The XYZ three-axis coordinate system is defined by the image sensor's optics and the plane of its CCD 16. Although suitable 3-axis coordinate systems may be determined for other possible imaging sensor optical configurations, as described for the embodiments herein the z-axis is coincident with the optical axis of the image sensor, and the XY plane is defined as parallel to the plane of its CCD 16. Thus, as described for these embodiments, the image sensor must be manufactured with its CCD mounted orthogonally to the image sensor's optical axis, which also must pass through, or very near to, the center of the CCD. The image plane 40 is, for technical convenience, placed in a position coincident with the spatial XY plane in the XYZ coordinate system.

Figure 5:
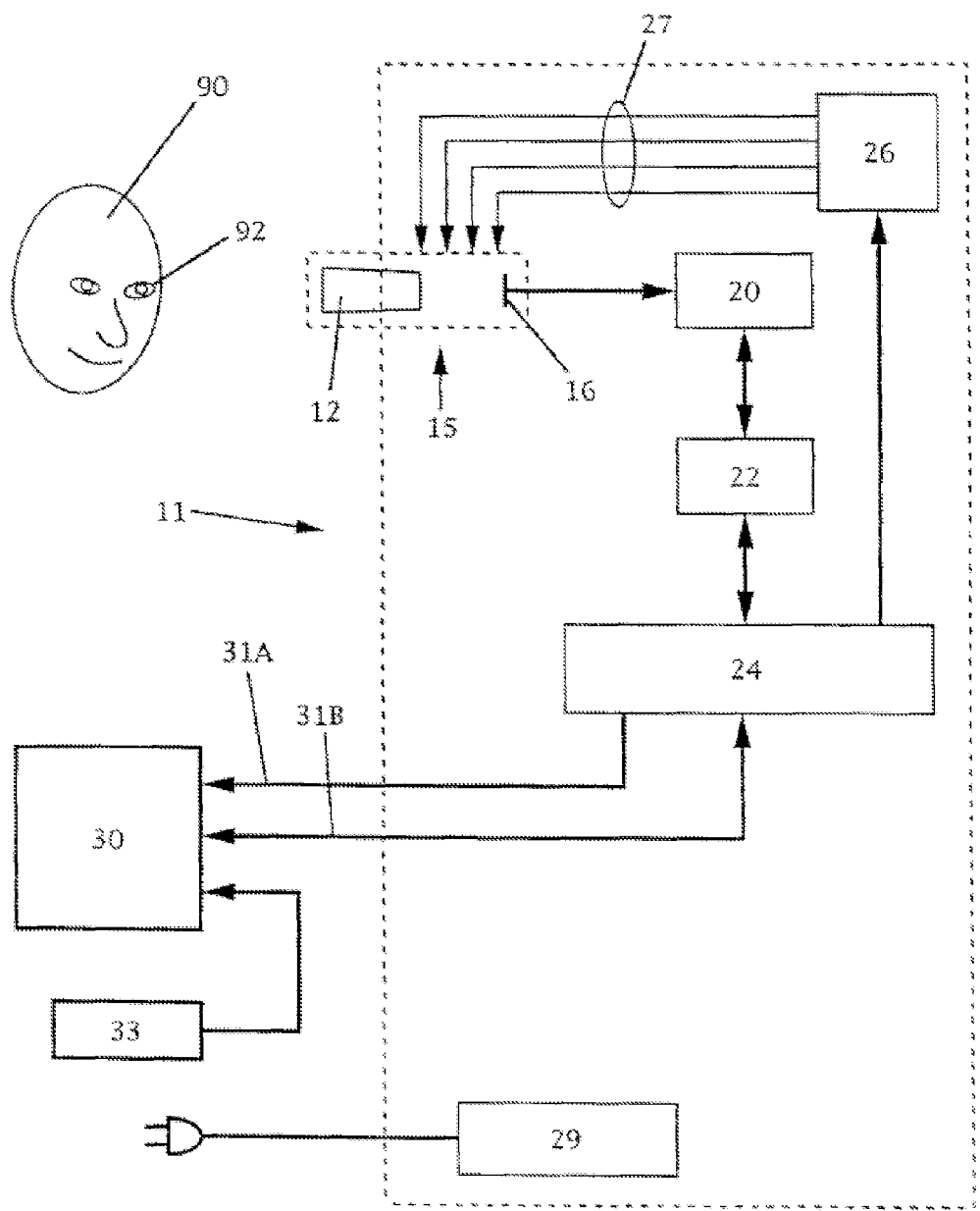
FIG. 5 is a system block diagram of a computing system suitable for implementing the various embodiments.

FIG. 5 is a block diagram of functional and structural elements within the digital camera 11, as well as connections to a personal computer 30. Inside the digital camera 11, a digital imager 15 provides digital images to an image processor 20 in the form of pixel array values. The image array size depends on the array size of the image sensor's CCD 16.

A CCD sensor used to collect images for the various embodiments may range in size from a few hundred pixels square to one to three thousand on a side, depending on physical constraints and the resolution required for a particular application. In an embodiment, for a camera configured as shown, a larger CCD array (e.g., 5-10 megapixels) will provide sufficient resolution over a relatively wide field of view to enable a user 90 to move his/her head in and out, back and forth, as comfort or inclination requires.

When exposed to light entering the digital imager 15 through lens 12, each pixel in CCD array accumulates an electric charge which is proportional to the intensity of the light incident upon that pixel. Each pixel's charge is gated (at a rate appropriate to the needs of the application) through an analog circuit which converts it to a voltage. The resultant voltage is proportional to the color or gray-scale value assigned to the intensity of the light falling upon that pixel. This series of gated pixel voltages is then sampled digitally and stored in memory 22 by the image processor 20. The color or gray-scale assigned to a particular intensity level is not absolute, and may depend upon the range of colors or gray-scales and light intensities allowed by the system.

Successive images may be obtained and operated on by the image processor 20. The image processor 20 may use standard image processing techniques well known in the art, such as filtering, thresholding, edge detection, segmentation, and pattern recognition to locate the user's eyes 92 within each image of the user's head 90. Such processed images may be passed to the control processor 24 which may implement the algorithms of the various embodiments. As described more fully below, such processing algorithms may determine the location and orientation of the irises of the user's eyes 92 within the image plane 40, mathematically determine the location and orientation of the optical axis vectors of each eye in the XYZ coordinates of the three-axis coordinate system, and use those vectors to determine the locations of the eyeball centers within the three axis coordinate system. Subsequent calculations may process the eyeball center location information sufficient to enable these determinations to be used as inputs to the computer 30. In an embodiment, a SCSI connection 31B between the control processor 24 in the digital camera 11 and the computer 30 may provide an interface to mouse emulator (as one example) control software running on the computer 30 which may serve to provide inputs to the computer based on the user's head position and orientation. In some implementations, the control processor 24 may be part of the computer 30, in which case there may be no need for cables 31 or a separate control processor 24.

In some implementations, the digital camera 11 may also include a power supply 29. The digital imager 15 may be controlled (e.g., over control lines 27) by a camera control interface 26 which may receive inputs from the control processor 24 or from the computer 30. Such camera control functions may include iris, focus, tilt and zoom.

Figure 6:
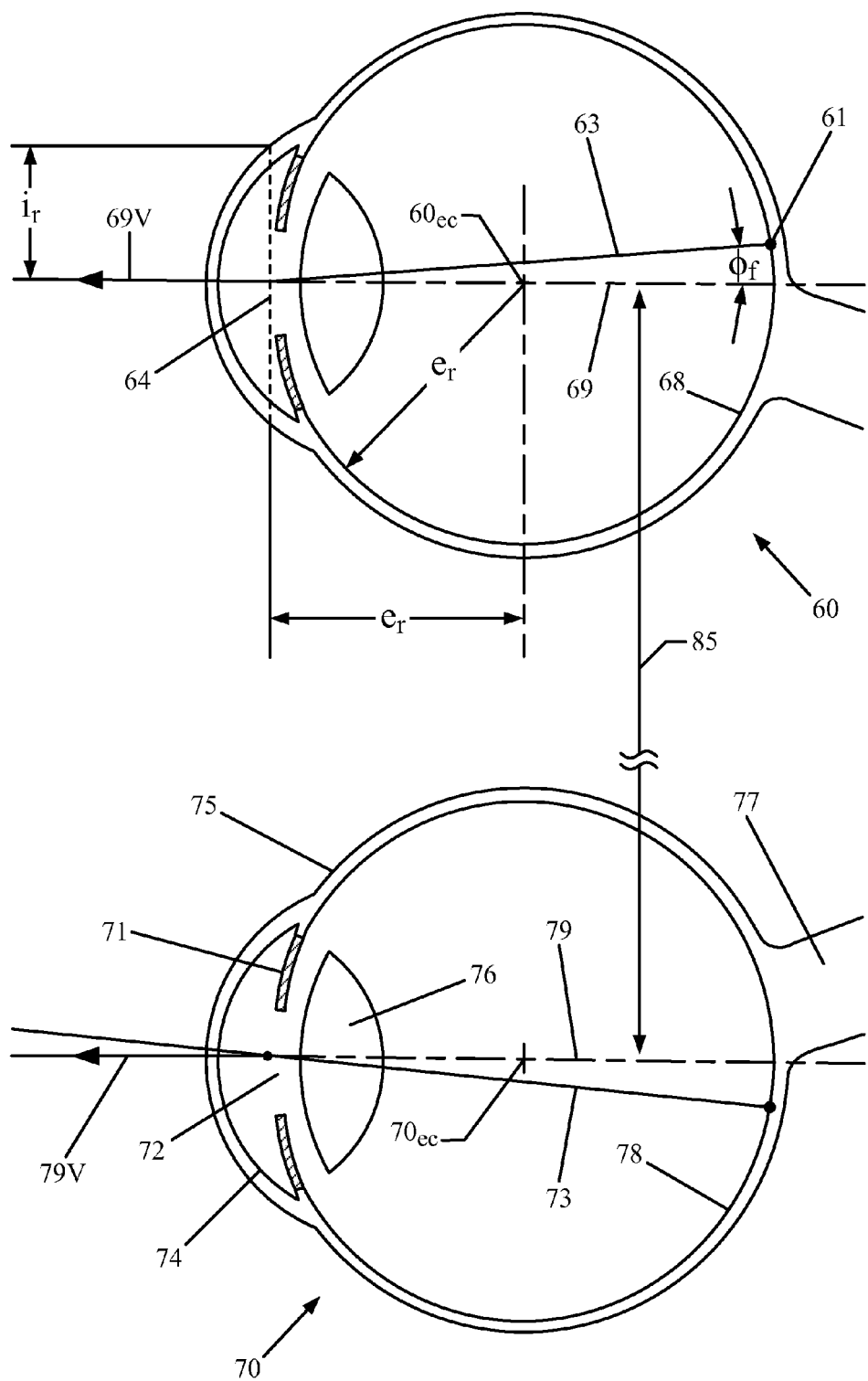
FIG. 6 is a schematic model of human eyes viewed from the top in cross-section showing measurements and vectors pertinent to the various embodiments.

FIG. 6 schematically illustrates model cross-sections of two human eyes, denoted generally as 60 and 70, which are used to explain the basis of the algorithms employed by the various embodiments. This eye model is primarily based upon Gullstrand's schematic eye, supplemented by generic physiological data. A few details are new, however, resulting from requirements unique to the embodiment methods. All of the features shown in the two cross-sections may be considered as lying in a single plane, as though a slice had been taken through an upright human head through the center of both eyes to reveal the details shown. Models shown for the right 60 and left 70 eyes are mirror images of one another. It should be noted that the inter-eyeball distance 85 is not to scale vis-à-vis the scale of the eyes 60, 70.

The illustration representing the left eye 70 shows the physiology of the human eye. The lens 76 is located just behind the iris 71 and the opening of the pupil 72. These structures are protected by the cornea 74. The sclera 75, or "white" of the eye, covers the eyeball from the edge of cornea 74 around to the optic nerve 77. Light entering the pupil 72 is gathered by the retina 78, which acts something like a CCD sensor in a digital camera, sending nerve impulses representative of images through the optic nerve 77 to the appropriate processors inside the human brain. Vision related axes include the optical axis 79 and the visual axis 73.

The illustration representing the right eye 60 shows the physical relationships between the optical axis 69, the visual axis 63, and the apparent iris disc 64 (as magnified slightly by the cornea). The fovea 61 is an area of the retina 68 where the retina's light gathering sensors are concentrated for increased resolution. As noted above, in this model, all four axes, i.e., the optical axes 69, 79 and visual axes 63, 73 of both eyes, lie in the same plane. Additionally, as shown in the illustration of the right eye 60, the optical axis 69 and the visual axis 63 intersect at the center point of the apparent iris disc 64. The optical axis 69 is orthogonal to the apparent iris disc 64, while the visual axis 63 extends from the fovea 61 through the center of the iris disc 64 to the object being viewed. In this illustration, $\Phi_f$, the angle between the optical and visual axes, $i_r$, the radius of the apparent iris disc 64, and $c_r$, the internal radius of the eyeball, represent values which differ slightly from individual to individual and are treated as variables for the discussion which follows.

Each eyeball 60, 70 is roughly spherical having an eyeball center point $60_{ec}$, $70_{ec}$ that remains generally fixed with respect to the skull. The left and right eyes 60, 70 are separated by an inter-eyeball distance 85, which in this model is measured between the two eyeball center points $60_{ec}$, $70_{ec}$. Since the eyeball center points $60_{ec}$, $70_{ec}$ remain generally fixed in position with respect to the skull, the inter-eye distance 85 defines a line of known length (following a calibration measurement with the user) which may be used to calculate or define head orientation along that particular axis once the eyeball center points $60_{ec}$, $70_{ec}$ are located in the three axis coordinate system using the embodiment methods described below.

Figure 7:
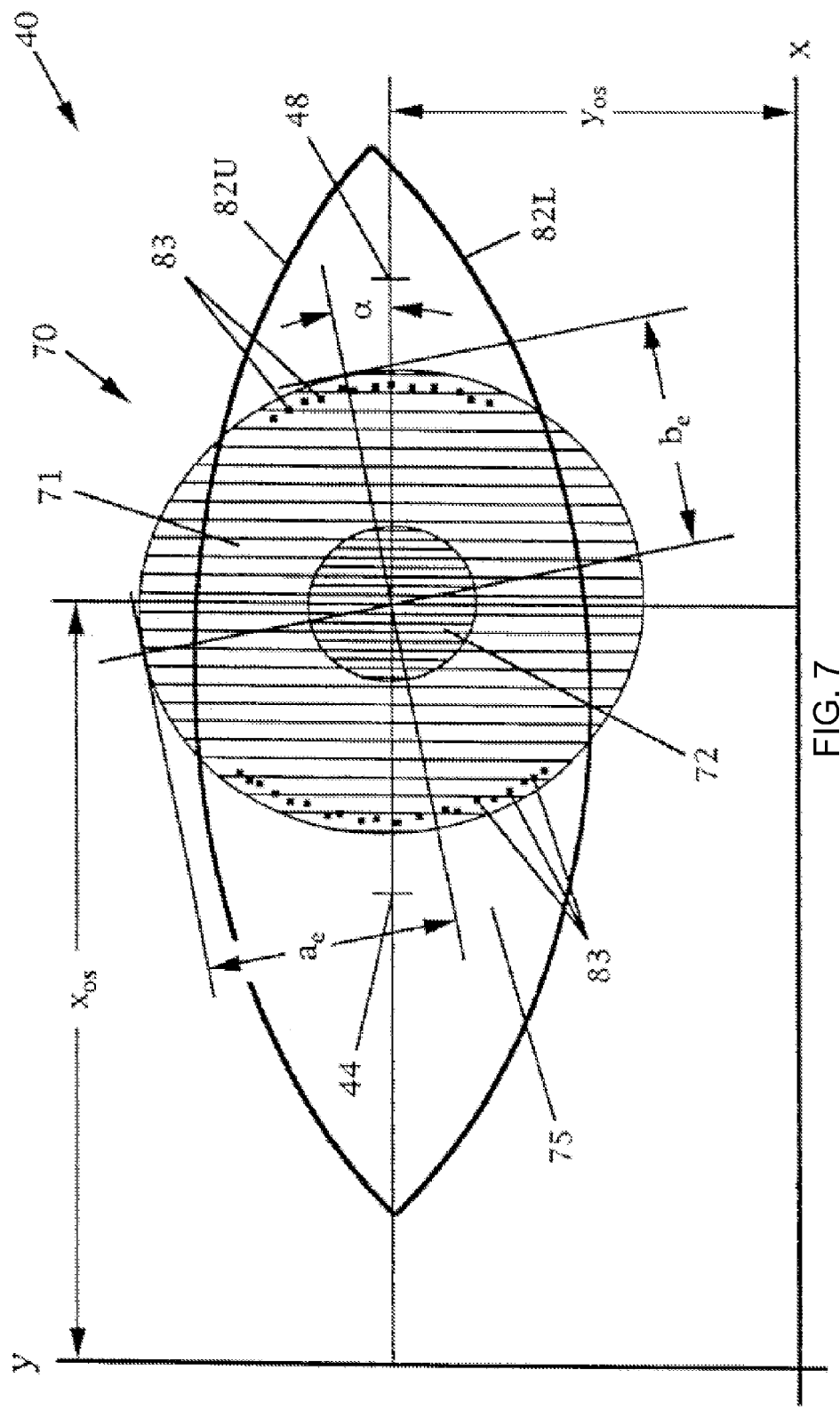
FIG. 7 is a diagrammatic view of an image of a user's left eye in a first quadrant of the image plane.

FIG. 7 is a diagram of an image a user's left eye 70 as might be captured by a digital camera 11 in an embodiment. In this figure, the eye 70 is visible between the upper eye lid 82U and the lower eye lid 82L. The sclera 75, iris 71, and pupil 72 are indicated. Portions of the iris 71 under the eye lids 82U, 82L, although not visible to a camera, are shown here for purposes of explaining the optical axis vector formulations used in the embodiments. The iris 71 and the pupil 72 will generally appear as an ellipse in such camera images, unless the optical axes of the user's eyes are parallel to the optical axis of the camera (defined as the z-axis of the 3-axis coordinate system), in which case the shape of the iris 71 and the pupil 72 will appear circular. The iris 71 in the image plane 40 corresponds to the apparent iris disc 64 in the model discussed above with reference to FIG. 6. The iris 71 has been modeled as a flat disc to simplify the algorithms which are described below. Unless the user's visual axes lie at angles greater than about 35° to the Z axis in the XYZ three-axis coordinate system defined above with reference to FIG. 4A, the iris in the image will appear as a well-defined, flat elliptic disc.

In the various embodiments, a processor (e.g., image processor 20 or control processor 24) is configured (e.g., with software instructions) to process digital images of a user's face to locate the eyes, and then process those portions of images to identify the edges of each iris. After an eye 70 has been located in the image plane by the image processor 20 or 24 using pattern recognition techniques well known in the art, the processor begins the task of pinpointing the iris boundary (i.e., the boundary between the iris and the sclera).

Figure 8:
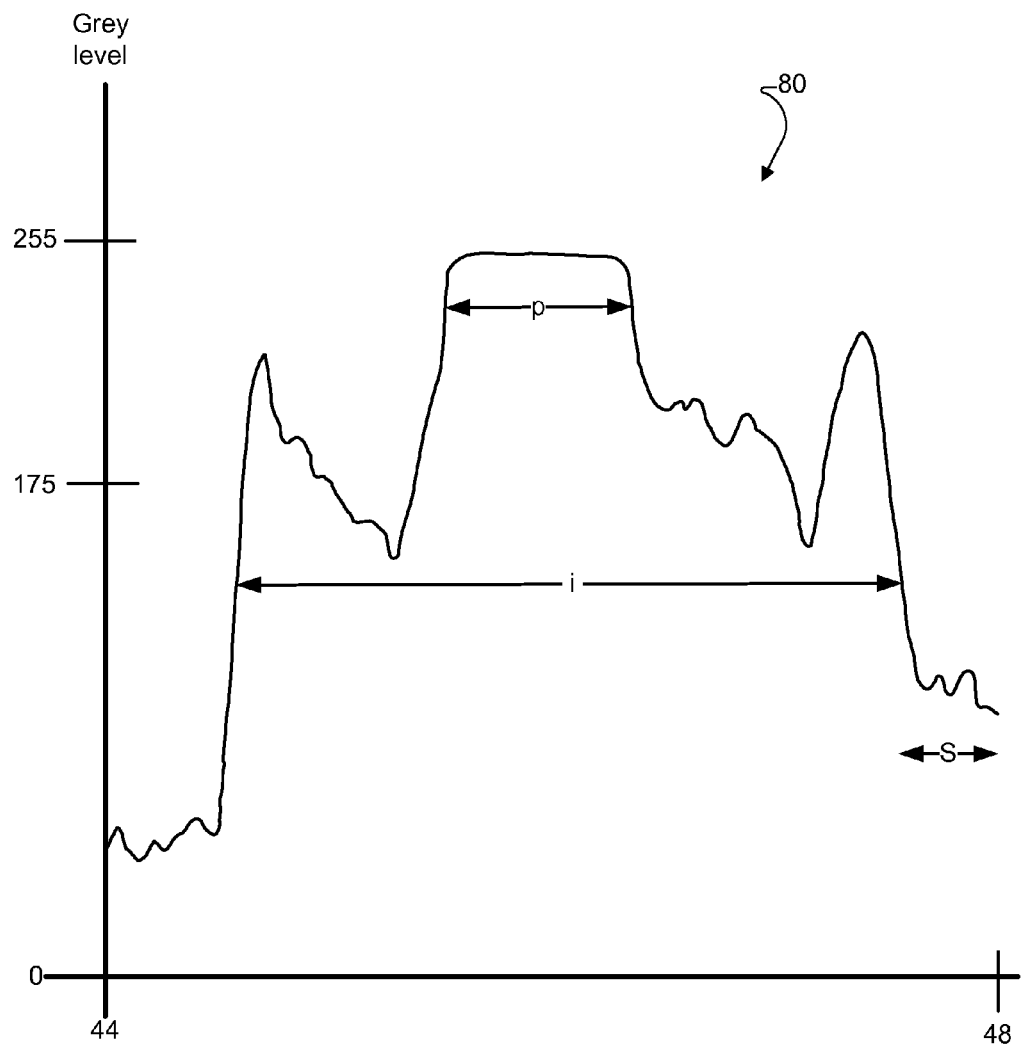
FIG. 8 is a plot of gray-scale values in an image scanning left to right across a human eye.

Since the sclera is white and the iris is typically much darker (e.g., brown or blue), this boundary may be recognized based upon the difference in color or gray-scale values between adjacent pixels. For example, if the gray-scale values of pixels lying along the line drawn between points 44 and 48 in FIG. 7 were plotted, the result would look something like the plot 50 shown in FIG. 8, which was taken from an actual gray-scale image of a human eye. In FIG. 8, the left scale is gray scale value, and the bottom scale represents pixel positions on the line between points 44 and 48.

The sections of plot 50 with gray-scale values representative of the sclera "s", the iris "i", and the pupil "p" are easily discernable. The variation in gray-levels between the outer edge of the iris and the pupil can be attributed to the "speckled" nature of the iris' coloring. The variation in mean gray-level between the sclera area near the left side 44 of plot 50 and the right 48 may be a result of shadowing by the eyelid and/or small differences in reflectance on the left and right sides of the iris. Notice that a relatively dark line of iris color, as indicated by the two outside peaks, circumscribes the iris, and offers recognizable point of reference for the iris boundary. Pixels nearest these peak values, or at points along the outer slope, e.g., at gray-level 175, may be selected algorithmically to represent the iris boundary. Given the contrast in gray-scale values between the iris and the sclera revealed in FIG. 8, known edge detection algorithms may be used to locate pixels representing the edges of the iris boundary as illustrated in FIG. 7.

Returning to FIG. 7, the process of recognizing pixel points on the iris boundary is continued along the visible iris boundary, taking care to avoid the secondary boundaries between the irises 71 and the upper 82U and lower 82L eyelids, until a sufficient number of boundary pixel points 83 are identified. As discussed below, these boundary pixel points 83 are used to determine the equation for an ellipse which most identically fits that of the iris 71 in the image using a least squares methodology. Thus, the number of boundary pixel points 83 that is sufficient may depend upon the desired or required level of accuracy in subsequent head position calculations. Depending on the resolution required by a particular application, these boundary pixel points 83 may be identified by single pixels located in the image plane by their X and Y distances from the origin (0,0), for example. If greater resolution is required than may be supplied by the CCD sensor in the system, another algorithm may be used to find inter-pixel points which are closer to the thresholds (e.g., peak values or slope) established for the conditions encountered.

The various embodiments use the diameter of a user's irises in calculating the optical axis unit vectors 69V, 79V of the user's eyes. Thus, either a direct measure of a user's iris diameters must be obtained or a diameter must be presumed. On average, humans have an iris diameter of approximately 12 mm, with deviation about this averaged value. For many user interfaces, relational position accuracy is all that is required. For these embodiments an average human iris diameter of 12 mm may provide sufficient relational position accuracy of the motion of the user's head when used in the various embodiment calculations. For some applications, such as user interfaces requiring greater accuracy, an accurate measure of the user's iris diameters may be required. Accurate measures may be obtained by direct physical measurement, such as by a researcher using sized templates held close to the user's eyes, and using his/her own judgment as to which template circle diameter most closely matches the user's irises. Alternatively, iris diameters may be measured indirectly, such as by using a calibration process in which an initial estimate of iris diameter is refined in order to improve the estimation of the optical axis vectors. In the discussion that follows, all processes, procedures, and calculations are indifferent as to whether the user's optical axis vectors are determined by using an iris diameter estimate, a relatively precise measurement of the user's irises, or by any other means.

The elliptic function for the iris boundary (as it appears in the image plane 40) is defined by five parameters: the x-offset ($x_{os}$) which is the X axis distance to the center of the iris ellipse; the y-offset ($y_{os}$), which is the Y axis distance to the center of the iris ellipse; $a_e$, which is ½ the length of the major axis $b_e$, which is ½ the length of the minor axis; and α, the rotation angle of the ellipse with respect to the X axis. These distances are in pixels since the ellipse fit is performed on pixel points in the image plane 40. All five of these ellipse defining parameters may be calculated using a least-squares fit of the general elliptic function to those boundary pixel points 83 identified by the algorithm discussed above.

These points are henceforth generically denoted by the couplet ($x_i, y_i$). The general elliptic function is defined as:

$$\frac{[\sin\alpha(y_i - y_{os}) + \cos\alpha(x_i - x_{os})]^2}{b_e^2} + \frac{[\cos\alpha(y_i - y_{os}) - \sin\alpha(x_i - x_{os})]^2}{a_e^2} = 1 \quad \text{Equation 1}$$

When simplified, this equation fits the form:

$$Ax_i^2 + Bx_iy_i + Cy_i^2 + Dx_i + Ey_i + F = 0 \quad \text{Equation 2}$$

where: $B^2 - 4AC < 0$. For the least-squares fit, this equation may be recast in the form:

$$y_i^2 = A'x_i^2 + B'x_iy_i + D'x_i + E'y_i + F' \quad \text{Equation set 3}$$

where:

$$A' = \frac{-(b_e^2\sin^2\alpha + a_e^2\cos^2\alpha)}{a_e^2\sin^2\alpha + b_e^2\cos^2\alpha} = -A/C$$

$$B' = \frac{-[(a_e^2 - b_e^2)\sin 2\alpha]}{C} = -B/C$$

$$D' = \frac{2Ax_{os} + By_{os}}{C} = -D/C$$

$$E' = \frac{2Cy_{os} + Bx_{os}}{C} = -E/C$$

$$F' = \frac{a_e^2 b_e^2 - Ax_{os}^2 - Bx_iy_i - Cy_{os}^2}{C} = -F/C$$

The five parameters defining the iris ellipse may be determined from a least-squares fit of the iris boundary points to this function. Fifty to a hundred points, spread along the boundaries on both sides of the iris, will provide excellent precision to support the embodiment algorithms.

From the list of boundary points $(x_i, y_i)$, the following calculations may be made:

$\Sigma y_i^2 = a$ $\Sigma x_i^2 = b$ $\Sigma x_i y_i = c$ $\Sigma x_i = d$ $\Sigma y_i = e$ $\Sigma y_i^3 = f$ $\Sigma x_i^2 y_i = g$ $\Sigma x_i y_i^2 = h$ $\Sigma x_i^3 = m$ $\Sigma x_i y_i^3 = p$ $\Sigma x_i^3 y_i = r$ $\Sigma x_i^2 y_i^2 = s$ $\Sigma x_i^4 = t$      Equation set 4 and # of pixel points=n.

For the least squares fit, the following five equations are required to solve for the five unknown coefficients, A', B', D', E', and F', from the general elliptic function:

$a = A'b + B'c + D'd + E'e + F'n$ $f = A'g + B'h + D'c + E'a + F'e$ $h = A'm + B'g + D'b'E'c + F'd$ $p = A'r + B's + D'g + E'h + F'c$ $s = A't + B'r + D'm + E'g + F'b$      Equation set 5

Solving this system of equations by elimination, the following lists of calculations may be performed:

$a' = fn - ae$ $b' = gn - be$ $c' = hn - ce$ $d' = cn - de$ $e' = an - e^2$ $f' = hn - ad$ $g' = mn - bd$ $h' = gn - cd$ $m' = bn - d^2$ $n' = pn - ac$ $p' = rn - bc$ $r' = sn - c^2$ $s' = sn - ab$ $t' = tn - b^2$ $a'' = e'f' - a'd'$ $b'' = e'g' - b'd'$ $c'' = e'h' - c'd'$ $d'' = e'm' - d'^2$ $e'' = e'n' - a'c'$ $f'' = e'p' - b'c'$ $g'' = e'r' - c'^2$ $h'' = e's' - a'b'$ $m'' = e't' - b'^2$ $a''' = d''e'' - a''c''$ $b''' = d''f'' - b''c''$ $c''' = d''g'' - c''^2$ $d''' = d''h'' - a''b''$ $e''' = d''m'' - b''^2$      Equation set 6

Further, solving:

$$A' = \frac{c'''d''' - a'''b'''}{c'''e''' - b'''^2}$$

$$B' = \frac{a''' - A'b'''}{c'''}$$

$$D' = \frac{a'' - A'b'' - B'c''}{d''}$$

$$E' = \frac{a' - A'b' - B'c' - D'd'}{e'}$$

$$F' = \frac{a - A'b - B'c - D'd - E'e}{n}$$

Equation set 7

Finally, by substituting:

$$2\alpha = \arctan[B'/(A'+1)]$$

$$y_{os} = \frac{2A'E' - D'(A'+1)\tan 2\alpha}{4A' + (A'+1)^2 \tan^2 2\alpha}$$

$$x_{os} = \frac{(A'+1)y_{os}\tan 2\alpha + D'}{-2A'}$$

$$a_e^2 = \frac{(F' - A'x_{os}^2 + y_{os}^2)\cos 2\alpha - (A'+1)x_{os}y_{os}\sin 2\alpha}{A'\sin^2\alpha + A'\cos^2\alpha}$$

$$b_e^2 = \frac{-\left[\begin{array}{c}(F' - A'x_{os}^2 + y_{os}^2)\cos 2\alpha - \\ (A'+1)x_{os}y_{os}\sin 2\alpha\end{array}\right]}{\sin^2\alpha + A'\cos^2\alpha}$$

Equation set 8

These solutions yield the location and orientation of the iris ellipse within the coordinate system of the image plane from the measurable parameters obtained by processing of the image of the user's head obtained by the digital camera. In all, the operations involved in solving these equations require fewer than 700 multiply and divide instructions for each eye, and even a slow processor performing one multiply or divide per microsecond requires less than one millisecond of realtime to complete these calculations.

Once the five parameters have been calculated for the iris ellipse, these parameters may be used to determine the location and orientation of the optical axis 79, which is defined by the optical axis vector 79V pointing out from the center of the apparent iris disc (i.e., the center of the pupil). An embodiment method for calculating the optical axis unit vectors 69V, 79V is described below; however, the claims are not limited to this method and other arithmetic algorithms may be employed for determining these vectors unless specifically recited in the claims. This method differs from that described in U.S. Pat. No. 5,471,542, which method is based upon an erroneous assumption that the two a-axis endpoints of any ellipse are equidistant from the origin (0, 0, 0). The error in this assumption is shown by the above discussion with reference to FIGS. 2 and 3. Further, while the method described in U.S. Pat. No. 5,471,542 will provide optical axis solutions for a user's eyes, these solutions may not possess enough accuracy to implement the embodiments herein or even those described in U.S. Pat. No. 5,471,542. The method described herein, on the other hand, is accurate, and may be employed to realize any embodiment.

In the embodiment method for calculating the optical axis unit vector 79V, it is necessary to first calculate positions (in the referenced XYZ coordinate system) for at least three points on the iris disc, including the center. Once these points are found, a simple cross-product of the vectors between the center of the disc and two other points on that disc will produce the optical axis unit vector 79V.

Figures 9A, 9B:
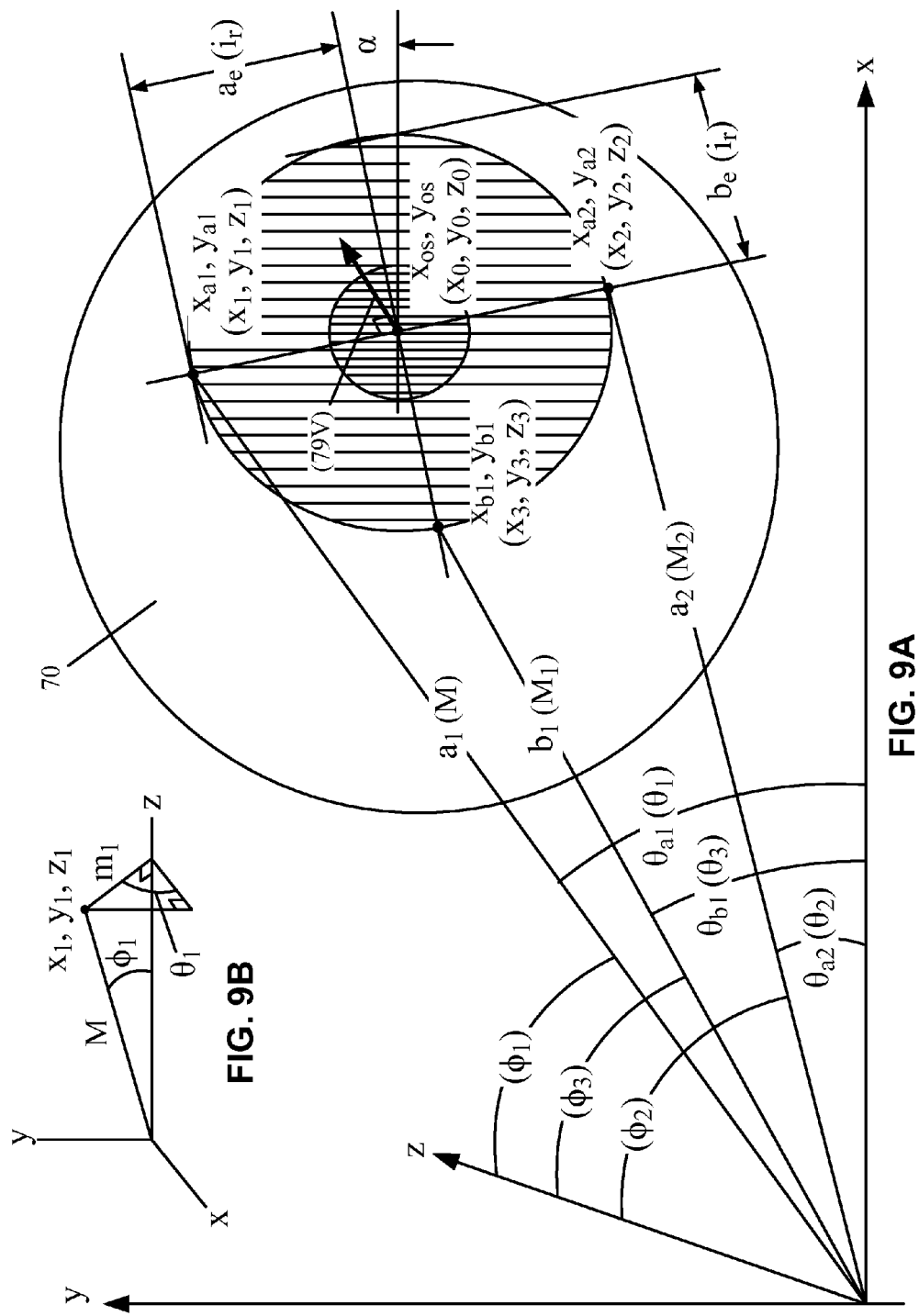
FIG. 9A is a diagram of an eye in the image plane.
FIG. 9B illustrates a point-of-gaze three-axis coordinate system which includes the image plane depicted in FIG. 9A.

FIG. 9A illustrates the left eyeball 70 (as it might appear magnified, and stripped of all surrounding tissue) in the image plane 40 of the digital imager 15 in a preferred embodiment. The Z axis has been added to serve as a reference to FIG. 9B. Note that four points, i.e., three on the edge of the apparent iris disc and one at the center, have been identified. Each point has been denoted by a coordinate couplet and triplet, e.g., $(x_{os}, y_{os})$ and $(x_0, y_0, z_0)$. The couplet associates the point to the image plane; the triplet associates the point to the XYZ coordinate system defined by the sensor's optical system. All symbols in FIG. 9A bounded by parentheses represent spatial values within the three-axis coordinate system. At the start of the calculation, none of the triplets are known. The couplet $(x_{os}, y_{os})$ is known. The other three may be easily calculated from the five iris parameters using trigonometry. For example, it is seen that: $x_{a1} = x_{os} - a_e \sin \alpha$, and $y_{a1} = y_{os} + a_e \cos \alpha$. The distance in the image plane (in pixels) between the origin (0,0) and each point on the edge of the apparent iris disc is simply the hypotenuse of the triangle formed by the point's X and Y coordinates: $b_1 = (x_{b1}^2 + y_{b1}^2)^{1/2}$, for example.

Because the axes in the image plane are placed as defined, i.e., coincident with the spatial x and y axes, and because the Z axis is defined as coincident with the optical axis of the image sensor, any line in the image which passes through the origin represents not only a distance measured in pixels, but also a spatial angle, i.e., one which can be directly related to the field-of-view of the image sensor's optics by some function, $f_{op}$. All of the distances $a_1$, $a_2$, and $b_1$ in FIGS. 9A and 9B, therefore, also represent unique angles in the XYZ three-axis coordinate system, as subtending between related rays $(M_i)$ and the z-axis.

FIG. 9B helps clarify the physical relationships that exist between one of the spatial points identified with the iris disc, $(x_1, y_1, z_1)$ in this case, and its corresponding point in the image plane, $(x_{a1}, y_{a1})$. FIG. 9B depicts point $(x_1, y_1, z_1)$ as located and measured in the image plane's attendant XYZ coordinate system. As shown, a right triangle can be constructed where the hypotenuse M connects the origin in the inset diagram with the point $(x_1, y_1, z_1)$, and where side $m_i$ intersects the Z axis at a distance $z_1$ from the origin (0,0,0). The projection of $m_1$ through the sensor's optics would produce line $a_1$ as it appears in the image plane. The spatial angle $\phi_1$ between M and the Z axis is therefore related to $a_1$ by $f_{op}$, i.e., $\phi_1 = f_{op}(a_1)$. Additionally, 1) the extended plane defined by this right triangle (M, $m_1$, Z axis) also contains line $a_1$, and 2) the XZ plane in the XYZ coordinate system also contains the X axis shown in the image plane. Therefore, the spatial angle $\theta_1$ formed by the intersection of these two planes is also equal to the plane angle $\theta_{a1}$ in the image plane formed by the intersection of $a_1$ and the x axis. The lines $a_2$ and $b_1$ are related to angles $\phi_2$, $\theta_2$, $\theta_{a2}$ and $\phi_3$, $\theta_3$, $\theta_{b1}$ in a similar fashion.

The iris disc in space is circular when its optical axis is parallel to the z-axis, not elliptic as it most always appears when projected into the image plane. Further, the distance in space between the two edge points $(x_1, y_1, z_1)$ and $(x_2, y_2, z_2)$ is equivalent to twice the iris radius $i_r$. Additionally, the spatial distance between $(x_o, y_o, z_o)$ and any of the edge points is identically $i_r$, and the distance between the b-axis edge point $(x_3, y_3, z_3)$ and either of the other two edge points is $\sqrt{2} i_r$. It is also clear, therefore, that:

$$i_r^2 = (x_1 - x_0)^2 + (y_1 - y_0)^2 + (z_1 - z_0)^2$$

$$i_r^2 = (x_3 - x_0)^2 + (y_3 - y_0)^2 + (z_3 - z_0)^2$$

$$2i_r^2 = (x_1 - x_3)^2 + (y_1 - y_3)^2 + (z_1 - z_3)^2$$

$$2i_r^2 = (x_2 - x_3)^2 + (y_2 - y_3)^2 + (z_2 - z_3)^2$$

$$4i_r^2 = (x_1 - x_2)^2 + (y_1 - y_2)^2 + (z_1 - z_2)^2 \qquad \text{Equation set 9}$$

Further, with reference to FIG. 9A, each of the coordinates which define a point in the image may be expressed in terms of M, an unknown, and the two known angles associated with each of them—$\phi_1$ and $\theta_{a1}$ for $a_1$; $\phi_2$ and $\theta_{a2}$ for $a_2$—thus:

$$x_0 = M_0 \sin \phi_0 \cos \theta_0 = A_{x0} M_0 \text{ (where } A_{x0} = \sin \phi_0 \cos \theta_0\text{)}$$

$$y_0 = M_0 \sin \phi_0 \sin \theta_0 = A_{y0} M_0$$

$$z_0 = M_0 \cos \phi_0 = A_{z0} M_0$$

$$x_1 = M_1 \sin \phi_1 \cos \theta_{a1} = A_{x1} M_1$$

$$y_1 = M_1 \sin \phi_1 \sin \theta_{a1} = A_{y1} M_1$$

$$z_1 = M_1 \cos \phi_1 = A_{z1} M_1$$

$$x_2 = M_2 \sin \phi_2 \cos \theta_{a2} = A_{x2} M_2$$

$$y_2 = M_2 \sin \phi_2 \sin \theta_{a2} = A_{y2} M_2$$

$$z_2 = M_2 \cos \phi_2 = A_{z2} M_2$$

$$x_3 = M_3 \sin \phi_3 \cos \theta_{b1} = A_{x3} M_3$$

$$y_3 = M_3 \sin \phi_3 \sin \theta_{b1} = A_{y3} M_3$$

$$z_3 = M_3 \cos \phi_3 = A_{z3} M_3 \qquad \text{Equation set 10}$$

Therefore, with reference to Equation set 9:

$$i_r^2 = (A_{x1} M_1 - A_{x0} M_0)^2 + (A_{y1} M_1 - A_{y0} M_0)^2 + (A_{z1} M_1 - A_{z0} M_0)^2 \qquad \text{Equation 11}$$

$$i_r^2 = (A_{x3} M_3 - A_{x0} M_0)^2 + (A_{y3} M_3 - A_{y0} M_0)^2 + (A_{z3} M_3 - A_{z0} M_0)^2 \qquad \text{Equation 12}$$

$$2i_r^2 = (A_{x1} M_1 - A_{x3} M_3)^2 + (A_{y1} M_1 - A_{y3} M_3)^2 + (A_{z1} M_1 - A_{z3} M_3)^2 \qquad \text{Equation 13}$$

$$2i_r^2 = (A_{x2}M_2 - A_{x3}M_3)^2 + (A_{y2}M_2 - A_{y3}M_3)^2 + (A_{z2}M_2 - A_{z3}M_3)^2 \quad \text{Equation 14}$$

$$4i_r^2 = (A_{x1}M_1 - A_{x2}M_2)^2 + (A_{y1}M_1 - A_{y2}M_2)^2 + (A_{z1}M_1 - A_{z2}M_2)^2 \quad \text{Equation 15}$$

This system of five quadratic equations in four unknowns may be solved in a variety of ways, the simplest of which appears to be reducing the equation set to three equations, carefully selected to provide a reasonably swift iterative solution. For example, the first three equations (11, 12 & 13) comprise such a set. If a reasonable first estimate of $M_0$ may be determined, the first two equations reduce to simple quadratics in a single unknown, which may then be factored, and the third equation may be employed to check the answers obtained. An iterative process may then be employed to successively reduce errors in the iterated solutions to arrive at the correct values for $M_0$, $M_1$, and $M_3$ relatively quickly. Likewise, the last three equations in set 11 (13, 14 and 15) comprise a similarly tractable set. Because these three equations measure the largest available "features" of the iris disc ellipse, this is the exemplary method described in detail herein.

In general, any solution algorithm requires a value for the iris radius $i_r$ to proceed. If the iris radius $i_r$ for this particular user is a value already known, such as a measured value stored in memory, then this value may be used to solve the equation set. If $i_r$ is not known, an estimated value, such as the value of the average human iris radius, may be used to solve the equation set.

As discussed above, Equation set 11 may be reduced to a system of three quadratic equations in three unknowns, which, in this example, comprise Equations 13, 14, and 15. To solve these relatively easily, an estimate of $M_3$ is needed, which renders Equations 13 and 14 simple quadratics in a single unknown, which can then be factored. To compute an estimate of $M_3$, the fact that length $a_e$ (in pixels) corresponds directly to $i_r$ (in mm) may be used. As discussed above with respect to FIGS. 2 and 3, when thought of as originating at (0,0) in the image, the pixel length of $a_e$ corresponds to a specific angle, $\phi_{ae}$, which may be calculated using Equation 0. This angle subtends a ray that may be thought of as intersecting a line of length $i_r$ in space extending from the z-axis outward, within a plane parallel to the XY plane, at a distance $z_{ae}$. It is a simple task to compute this distance thus:

$$z_{ae} = i_r / \tan \phi_{ae} \quad \text{Equation 16}$$

And (since $z_i = M_i \cos \phi_i$):

$$M_3 \approx z_{ae} / \cos \phi_3 \quad \text{Equation 17}$$

This distance is a reasonable first estimate of M3, and will serve as the starting point for the iterative process outlined by Equations 11-15. First, this initial estimate of M3 is substituted into Equation 13 and solved:

$$2i_r^2 = (A_{x1}^2 + A_{y1}^2 + A_{z1}^2)M_1^2 - 2M_3(A_{x1}A_{x3} + A_{y1}A_{y3} + A_{z1}A_{z3})M_1 + (A_{x3}^2 + A_{y3}^2 + A_{z3}^2)M_3^2,$$

where $$B_1 = (A_{x1}^2 + A_{y1}^2 + A_{z1}^2)$$

$$C_1 = 2M_3(A_{x1}A_{x3} + A_{y1}A_{y3} + A_{z1}A_{z3})$$

$$D_i = (A_{x3}^2 + A_{y3}^2 + A_{z3}^2)M_3^2 - 2i_r^2, \text{ and}$$

$$M_1^2 - (C_1/B_1)M_1 + D_1/B_1 = 0.$$

This equation is factored to find the roots ($M_{11}$, $M_{12}$), either one of which may be the correct $M_1$. The same process may be employed to solve Equation 14 for $M_2$, and check all four root combinations ($M_{11}/M_{21}$, $M_{12}/M_{21}$, $M_{11}/M_{22}$, $M_{12}/M_{22}$) using Equation 15. One of the four combinations will produce a result for Equation 15 which is closer than the other three to the value of $4i_r^2$. If this result equals $4j_r^2$ (or very nearly equals to the degree required for the application), the computation is complete and the correct values for $M_1$, $M_2$, and $M_3$ have been found. Otherwise, the estimate for $M_3$ may be iterated and may proceed in the same manner until a result for Equation 15 equals $4i_r^2$, which result is accomplished with the correct values for $M_1$, $M_2$, and $M_3$. Since the progression of $M_3$ estimates demonstrated predictable outcomes during development of this method, relatively few are needed to arrive at a result sufficiently identical to $4i_r^2$, assuming a reasonably sophisticated algorithmic process.

Using Equation set 10, along with the computed values of $M_1$, $M_2$, and $M_3$, the spatial coordinates associated with these points in the image $(x_1, y_1, z_1)$, $(x_2, y_2, z_2)$, $(x_3, y_3, z_3)$ may be determined. Since the disc center point is halfway between the two a-axis endpoints, $(x_1, y_1, z_1)$ and $(x_2, y_2, z_2)$, the disc center point $(x_0, y_0, z_0)$ may be determined.

$$x_0 = (x_1 + x_2)/2$$

$$y_0 = (y_1 + y_2)/2$$

$$z_0 = (z_1 + z_2)/2 \quad \text{Equation set 18}$$

Using $(x_0, y_0, z_0)$, $(x_1, y_1, z_1)$ [or $(x_2, y_2, z_2)$], and $(x_3, y_3, z_3)$, the iris disc vector associated with $(x_0, y_0, z_0)$ may be computed, which is the cross product of the vector from $(x_0, y_0, z_0)$ to $(x_1, y_1, z_1)$ and the vector from $(x_0, y_0, z_0)$ to $(x_3, y_3, z_3)$. This iris disc vector is the optical axis vector for that eye of the user, as seen in the image.

Using the algorithms described above to obtain the optical axis vectors of a user's eyes, the centers of the eyeballs may be calculated. If the eyeball radius $e_r$ is known, the eyeball center point $70_{ec}$ is simply the point on the optical axis unit vector 79V projection 102 into the eyeball that is one radius $e_r$ distance from the pupil. If the eyeball radius $e_r$ is not known, it may be readily calculated based on the calculated optical axis vectors.

Figure 10:
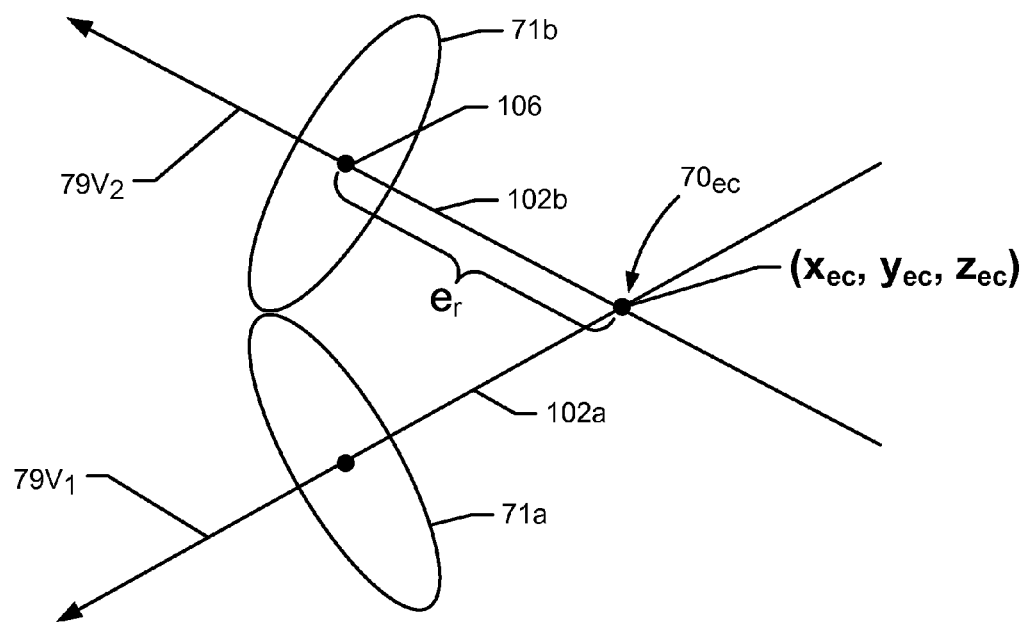
FIG. 10 is a diagram illustrating how the center of an eyeball is calculated by determining an intersection of the optical axis vectors resulting from the user looking in two different directions.

Referring to FIG. 10, the eyeball center point $70_{ec}$ may be identified as the intersection of all optical axis vectors determined when the user is gazing in different directions with the head held still. Using methods described above, the optical axis vectors $79V_1$, $79V_2$ may be determined for at least two discrete iris disc $71_a$, $71_b$ positions or gaze directions as illustrated in FIG. 10. These different vectors $79V_1$, $79V_2$ may be stored in memory and then compared to define a common point or intersection that constitutes the eyeball center $70_{ec}$. In order to increase the accuracy of the center location determination, several optical axis vectors $79V_1$, $79V_2$ may be determined for widely displaced gaze angles. For example, the user may be seated at a calibration station or rest his/her chin on a calibration stand that holds the head still during the process. A display may be employed to prompt the user to look at various spots on the screen in order to alter the user's gaze point. Such gaze targets may be presented on the screen in order to obtain a plurality of iris disc positions reflecting gaze points on the screen which differ widely (e.g., the display's left edge, along the centerline, right edge, top and bottom edges, and the four corners). Widely differing gaze points will provide optical axis vectors with relatively large solid angle differences. During this process, the user's head must be kept relatively still. This could be accomplished by asking the user to rest his/her chin upon a brace of some kind, or to place his/her head in a mechanical fixture of some kind However, the embodiment methods are robust enough to tolerate some small motion of the user's head, so that merely instructing the user to keep his/her head still may provide a sufficiently accurate result. Since the process requires very brief images, the process may be accomplished relatively quickly. Typically, this method for calculating the eyeball radius will be incorporated in an initial calibration procedure for each user. Nevertheless, this method is equally compatible with adaptive techniques, which could be employed to calculate a user's eyeball radius on the fly, refining the retained value as small errors (e.g., due to the user's indeterminate motion) are reduced over time. Using an initial calibration procedure may mitigate indeterminate motion by the user, resulting relatively rapidly in an accurate radius value calculation.

When the collected optical axis vectors $79V_1$, $79V_2$ are extended mathematically within the volume occupied by the user's eyeball (i.e., beneath the visible surface of the eye shown as vector portions $102_a$, $102_b$), the vectors will appear to intersect at, or very near to, a single point in space. This point may be presumed to indicate the position of the eyeballs center point $70_{ec}$. Considering the minor errors pertaining to any particular optical axis calculation (e.g., eyelids may be more open or more closed, different iris edge points are used for widely differing gaze points, etc.), it is unlikely that any two optical axis extension lines $102_a$, $102b$ will precisely intersect. Therefore, in order to find a single point nearest to the intersection for all of the collected extension lines, statistical analysis or a "bundling" function or similar process may be employed to identify a single most likely center point. An exemplary bundling function is disclosed in "SBA: A Software Package for Generic Sparse Bundle Adjustment," by Manolis I. A. Lourakis and Antonis A. Argyros, Transactions on Mathematical Software, Vol. 36, No. 1, Article 2, March 2009. That article describes a publicly available C/C++ software package which performs a highly efficient sparse bundle adjustment for sets of data similar to a collection of optical axis vector extension lines. Other similar functions and processes may be used to find the eyeball center point from a collection of optical axis vectors. Whichever function or process is employed, the output is a best estimate of the three-axis position of the eyeball center ($x_{ec}$, $y_{ec}$, $z_{ec}$).

Once the eyeball center point $70_{ec}$ ($x_{ec}$, $y_{ec}$, $z_{ec}$) has been found, the distance from that point to the origin point (e.g., the center of the pupil 106) for one or more of the collected optical axis vectors may be averaged to obtain the radius value $e_r$ for the user's eyeball. Once the eyeball radius $e_r$ is obtained, the value may be stored in memory and used to find the eyeball center point $70_{ec}$ for any subsequent iris disc position based on a calculated optical axis vector, whether or not the user's head has moved, and wherever the user is looking at the time. To do this, a line segment originating at the pupil may be extended along the optical axis vector extension lines $102a$, $102b$ by the length of the radius value $e_r$ to find the eyeball center point $70_{ec}$. In this manner, successive eyeball center points $70_{ec}$ may be tracked over time in order to track the motion of the user's head.

Since the eyeball center points $60_{ec}$, $70_{ec}$ remain a fixed distance apart, i.e., inter-eye distance 85, defining a line across the user's head, the calculations of the eyeball centers using these methods provides a robust and reliable measure of a user's head position with respect to left/right rotation, left/right tilting, and even up/down motion. Although sequential relational positioning of these eyeball centers is certainly adequate to embody many user interfaces—a cursor on a display, for example—well known facial recognition methods may be further used to determine a user's chin position (e.g., position of the chin with respect to the user's eyeballs) in order to more accurately track up/down (e.g., nodding) head orientation and motions. Whether by means of eyeball centers only, or together with other facial cues such as chin position, accurate tracking of head position may be used for a wide variety of applications. Some examples of useful applications include providing a hands-free mechanism for providing input commands to a computer, such as to move and control a cursor on a display screen, a telerobotic sensor for providing directional commands to cameras in a telerobotic system, tracking user head movements for scientific and medical studies, and monitoring operators of heavy equipment and automobiles to confirm their attention is properly focused. In general, any system that can benefit from accurately determining head position information may use the various embodiments. Thus, while the embodiments are described with reference to an example computer system, these descriptions are not intended to limit the scope of the claims.

The computational methods described above can easily be implemented within a variety of computing devices that couple to or include a digital camera positioned to image a user. In overview, such methods will involve obtaining an image of the user's face, such as while the user is using a computing device, locating the user's eyes and identifying the boundary of the user's iris in each image. Then, using the equations described above, the computing device can process the portion of the user's image including the irises using known or estimated iris diameters and previously determined eyeball diameters in order to locate the centers of the user's eyeballs. With the eyeball centers located in a three-axis coordinate system, various computerized methods may then determine a location and orientation of the user's head, which may be used as an input, such as to control position of a cursor or selection tool.

Figure 11:
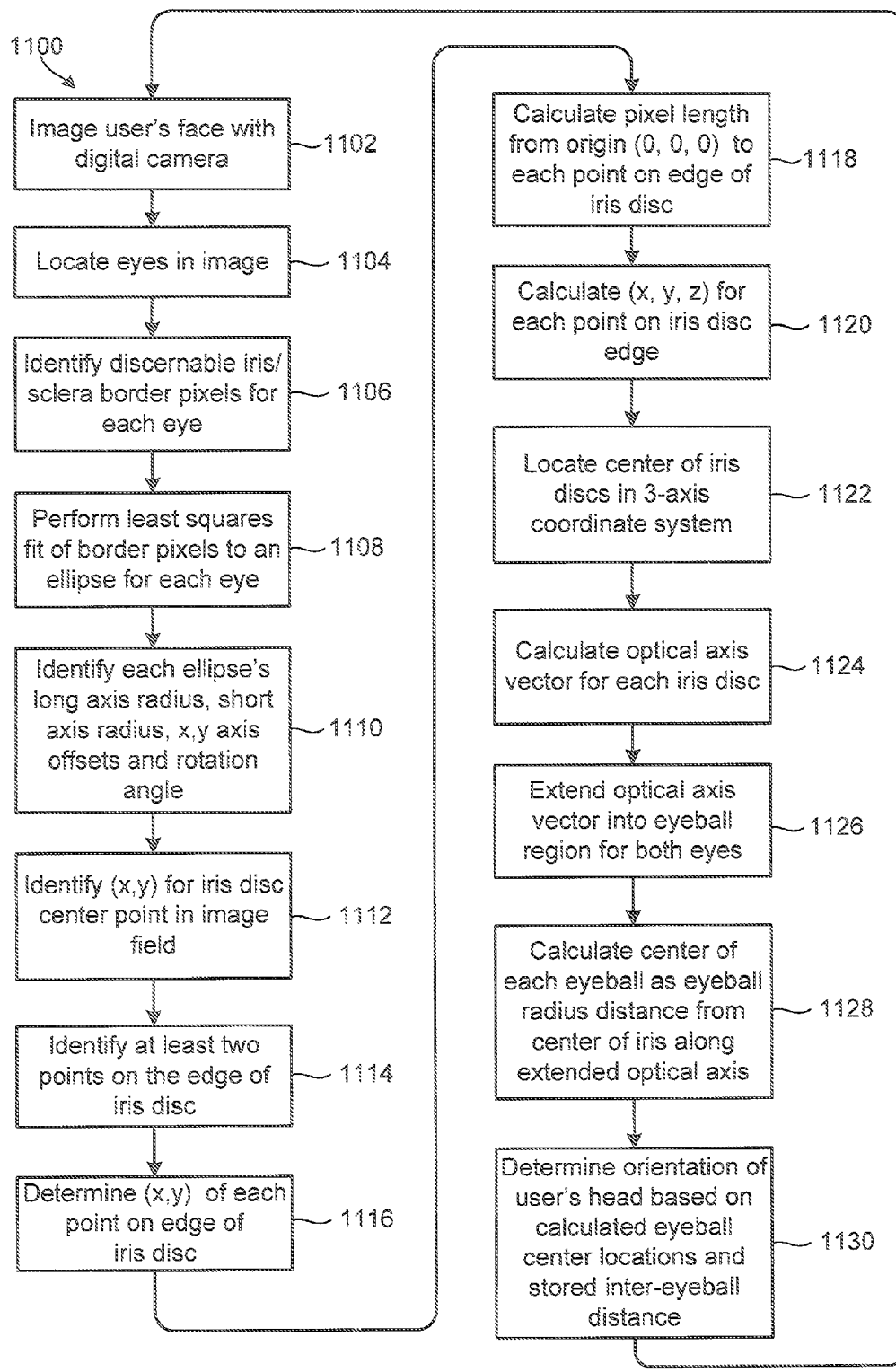
FIG. 11 is a process flow diagram of an embodiment method for determining a location and relative motion of a user's head by calculating the locations of the center of the user's eyeballs based on successive images of the user's face.

An embodiment method 1100 for determining a location and orientation of the user's head when the iris diameters and eyeball diameters are known or presumed is illustrated in FIG. 11. In various embodiments, the iris radius (or diameter) and eyeball spherical radius (or diameter) may be presumed or measured values which are stored in memory. FIG. 13 illustrates an example method for obtaining measurements of these values, which may be obtained in a calibration routine and then used in the method 1100 of determining the user's head orientation illustrated in FIG. 11. In method 1100 in step 1102, a digital camera may be used to obtain a digital image of the user's face. In step 1104, the obtained image may be processed normally to locate the eyes of the user within the image. Any known method for locating the eyes of an individual within a digital image may be used for this process. In step 1106, the portion of the obtained image containing the user's eyes may be processed to identify the discernible portion of the iris-sclera boundary (i.e., that portion not covered by the eyelids). Since the sclera is white and the iris is another color (i.e., brown, blue, green, or violet), this boundary identification step may use any of a number of image processing techniques to identify pixels at or near an abrupt color or gray-shade transition. This process may also involve pixel section algorithms to select those pixels in the obtained image which best represent the iris-to-sclera boundary. Further, this process may identify numerous pixels within the obtained user image which best correspond to the iris-to-sclera boundary, such as illustrated in FIG. 7.

In step 1108, a processor of the computing device may perform a least squares fit of the identified iris-to-sclera boundary pixels to an ellipse equation in order to identify the ellipse defining parameters in step 1110. Such ellipse defining parameters may include the ellipse long axis radius, short axis radius, X and Y coordinates of axis offset locations, angle of rotation and axis of rotation (i.e., line coordinates of the long axis). In step 1112 the processor may identify the (x, y) coordinates of the center point of the apparent iris disc in the image field, which are equal to the coordinates of axis offset locations ($x_{os}$, $y_{os}$). In step 1114, the (x, y) coordinates of at least two points on the edge of the apparent iris disc may be calculated using the ellipse defining parameters from step 1110. In step 1116, the distance in pixels between the origin (0,0) and each point on the apparent iris disc edge in the image plane may be calculated as the hypotenuse of the triangle formed by the (x, y) coordinates of the point. In step 1118, the pixel length of a ray from the origin (0,0,0) to the points on the iris disc edge may be determined using the iris radius and the spatial angle between the ray and the Z-axis, as described above in detail with respect to FIGS. 9A and 9B. In step 1120, the spatial coordinates (x, y, z) of the points on the iris disc edge may be calculated. In step 1122, assuming points on the iris disc edge are positioned so that a line between them is the iris diameter, the spatial coordinates of the center point of the iris disc may be calculated (since the iris disc is a circle in space, not an ellipse as it generally appears when projected into an image). In step 1124, the iris disc vector may be calculated as the cross product of the vector from ($x_0$, $y_0$, $z_0$) to ($x_1$, $y_1$, $z_1$) and the vector from ($x_0$, $y_0$, $z_0$) to ($x_3$, $y_3$, $z_3$).

These calculations determine the orientation and location of the iris disc in the three axis coordinate system. In step 1126, the processor extends the calculated optical axis vector into the eyeball region. Given the geometry of the eyeball, this line passes through the center of the eyeball, as illustrated in FIG. 6. Using a known or presumed radius of the eyeball, the center of the eyeball may be calculated in the three axis coordinate system in step 1128 as the distance from the center of the iris along the extended optical axis vector calculated in step 1126. Completion of the calculations through step 1128 locates the center of the eyeball within the three axis coordinate system defined by the digital camera that is illustrated in FIG. 4A.

Steps 1104 through 1128 may be performed by the computing device processor for both eyes—and may be performed for both eyes more or less in parallel—in order to determine the location of both eyeball centers within the three axis coordinate system. As a result of these calculations, the computing device processor will have the three-axis coordinates of two points within the head of the user that do not vary with expression or gaze angle, and thus accurately reflect the location and orientation of the user's head in space with respect to the digital camera. This information may be used in step 1130 to determine the orientation of the user's head within the three axis coordinate system. Using the two eyeball center points, the processor can determine user head position in terms of X, Y, Z location, right/left rotation, up/down motion, and left/right tilt angle. If a more accurate up/down rotation orientation is required by an application, such vertical head rotation may be determined using known facial recognition techniques which may image the top of the head or bottom of the chin (or other anatomical feature), which may be compared to the line between the two eyeball centers.

The process of steps 1102 through 1130 may be repeated frequently, such as by imaging the user's face a few times per second, in order to provide continuous inputs into the computing device.

Figure 12:
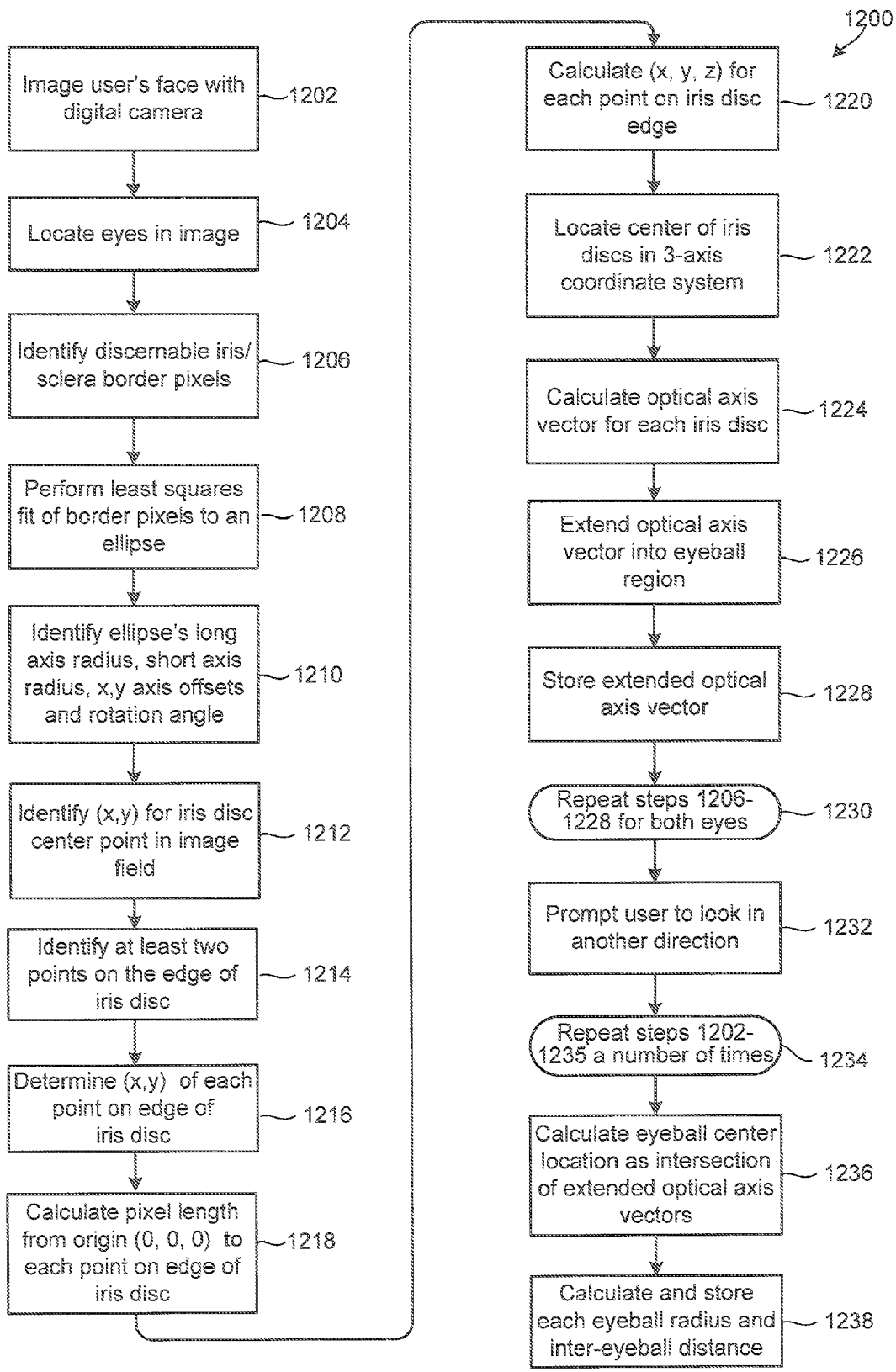
FIG. 12 is a process flow diagram of an embodiment method for calculating the radius of an eyeball and the inter-eyeball distance of a user based on an image of the user's face.

As mentioned above, a key factor in determining the center of the user's eyeballs is the radius of each eyeball. This value may be determined in a calibration operation, such as by implementing a method like that illustrated in FIG. 12. In method 1200 at step 1202, the user's face may be imaged by a digital camera, and a processor of the computing device may analyze the image to locate the eyes in step 1204. Similar to embodiment method 1100 described above, the obtained user image may be further processed to identify the discernible iris-to-sclera border pixels in step 1206. Performing a least squares fit of the iris-to-sclera border pixels to the ellipse equation in step 1208, the processor may identify the iris ellipse long axis radius, short axis radius, X and Y axis offsets and rotation angle in step 1210.

In step 1212, the processor may identify the (x, y) coordinates of at least two points on the apparent iris disc edge in the image field, which are equal to the coordinates of the axis offset locations ($x_{os}$, $y_{os}$). In step 1214, the distance in pixels between the origin (0,0) and each apparent iris disc edge in the image plane may be calculated as the hypotenuse of the triangle formed by the (x, y) coordinates of the point. In step 1216, the pixel length of a ray from the origin (0,0,0) to the points on the iris disc edge may be determined using the iris radius and the spatial angle between the ray and the Z-axis, as described above in detail with respect to FIGS. 9A and 9B. In step 1218, the spatial coordinates (x, y, z) of the points on the iris disc edge may be calculated. In step 1220, assuming the points on the iris disc edge are positioned so that a line between them is the iris diameter, then the spatial coordinates of the center point of the iris disc may be determined. In step 1222, the iris disc vector may be calculated as the cross product of the vector from ($x_0$, $y_0$, $z_0$) to ($x_1$, $y_1$, $z_1$) and the vector from ($x_0$, $y_0$, $z_0$) to ($x_3$, $y_3$, $z_3$). In step 1224, the processor may calculate the optical axis vector of the iris disc and, in step 1226, the optical axis vector may be extended into the eyeball region. In step 1228, the extended optical axis vector may be stored in memory, such as by storing the three-dimensional endpoint coordinates or by storing the three-dimensional coordinates of a point on the vector along with the three-dimensional vector tensor coordinates. In step 1230, the processor may repeat steps 1206 through 1228 for the other eye. As discussed above, the processing of the images of both eyes may proceed more or less in parallel.

In step 1232, the processor may display or audibly prompt the user to look in another direction so that another optical axis vector may be calculated. For example, the processor may generate a new target on the display and prompt the user to gaze at it. In step 1234, the processor may repeat steps 1202 through 1235 to obtain another image of the user's face and from that determine and store the extended optical axis vector. This process may be repeated a number of times in order to obtain a statistically relevant number of calculated optical axis vectors. Since the center of the eyeball remains approximately fixed, every optical axis vector should pass through the same center point. Therefore, in step 1236, the stored optical access vectors may be combined to locate the eyeball center as the intersection of each of the extended optical access vectors. As described above with reference to FIG. 10, this calculation may involve statistical analyses to identify a most likely center point within each eyeball based upon all of the calculated vectors. In step 1238, the location of the eyeball center may then be used to calculate the radius of each eyeball, as well is the inter-eyeball distance. The eyeball radius may be calculated as the distance between the plane of the iris disc and the eyeball center. The calculated eyeball radius and inter-eyeball distance may be stored in memory for use in the various embodiment methods as described above with reference to FIG. 11.

As mentioned above in the discussion of FIG. 10, the calibration operation of method 1200 may be accomplished while requiring the user to maintain his/her head in a fixed position, such as resting on a chin rest or similar structure. Since the processing of images may take place after the user face images have been obtained, this procedure may be accomplished quickly by performing steps 1202 and 1232 together in rapid sequence to obtain a series of images, after which the sequence of images may be processed (i.e., by the processor performing steps 1204 through 1230) in order to obtain a number of calculated extended optical axis vectors.

In an alternative application of the calculations described above, optical axis vectors and the eyeball center points of a user's eyes may be used to determine the visual axes of the user's eyes. The point of intersection of the two visual axes defines the user's instantaneous point-of-gaze, which is relationally stable with respect to the center points of the user's eyeballs and the optical axes. Further, XYZ offset distances from the eyeball center points remain constant, and may be calculated for each of the user's eyes. Once determined, the offset distances from the eyeball center points may be used to determine points that iteratively define successive visual axes. Alternatively, solid angle offset constants from the optical axes, derived in a similar manner, may be used to iteratively determine the user's visual axes over time.

As explained above, rapid saccadic motion argues against the use of point-of gaze as the primary mediator for a user interface. However, when focused by the user on a particular object or image feature, point of gaze may provide an accurate indication of the user's intent. In the various embodiments, point-of-gaze may serve as a user interface, or as one component thereof, when focused by the user on a particular object or image feature. For example, in a user interface that controls a computer cursor by head motion, as described above, the user's point-of-gaze may be implemented as a mouse click function. Thus, a computer mouse may be emulated by a user's head movement directing the cursor, and the user's point-of-gaze may select a "clickable" feature on a computer display screen by remaining fixed on the feature for a short duration (yet long enough to differentiate it from the saccadic background). Other user interface application embodiments may include virtual reality, augmented reality, head-up displays, etc.

As described above with respect to the embodiments tracking a user's head movements, the optical axis vectors and the eyeball center points of a user's eyes may be determined, whether or not the user's iris diameters are precisely known. An average diameter such 12 mm may be used, in which case head motion (as mediated by tracking the user's eyeball centers) is considered relationally accurate rather than physically accurate. Relationally accurate head motion may be used, for example, to reliably and smoothly control a cursor on a display screen. However, any constant error in the iris diameter metric, such as when an average is used, will position the user's optical axis vectors and eyeball center points nearer to, or farther from, the imaging sensor than they actually are. Consequently, the user's point-of-gaze will appear to converge either behind, or in front of, the object of the user's actual point-of-gaze, which may introduce enough uncertainty (between two clickable features, for example) to make operation unreliable. Reliability may be significantly improved by ensuring that the point-of-gaze is fixed upon a selectable feature, which has been separately indicated by means of the cursor before emulating the click function.

In an embodiment, an initially accurate measure of the iris may be used to produce a relatively accurate point-of-gaze in a single pass. Alternatively, when the user's iris diameter measurements are not known, an initial calibration process may be performed using an average diameter. Alternatively, when the user's iris diameters are not known, initial estimated diameters may be used and then calibrated in successive passes using targets at known locations in the user's visual field, as discussed above with respect to FIG. 14. Optimally, each target may be displaced from the others in a manner that causes relatively large solid angle displacements between the user's optical axis vectors as the targets are successively viewed. Suitable targets may be readily rendered upon a computer display that lies within the user's field of view, as long as the placement, position, and orientation of this display are defined within the coordinate system to a sufficient level of precision. Similarly, a user's visual axes may also be determined from a similar calibration process.

The user's optical axis vectors may be calculated from the iris diameter measurements, as discussed above with respects to FIGS. 9A and 9B. As discussed above, the user's eyeball center points may be determined within the 3-axis coordinate system defined by an imaging sensor's optics when the positions in the coordinate system of objections/targets being viewed are known. As discussed above with respect to FIG. 12, eyeball radius and inter-eye distance may be determined based on an image of the user's face. Using the algorithms described above to obtain the optical axis vectors of a user's eyes, the center points of the eyeballs may be calculated. If the eyeball radius of an eye is known, the eyeball center point may be determined as the point on the optical axis vector projection into the eyeball that is one radius distance from the iris disc center point.

A user's point-of-gaze may be determined from determining the instantaneous visual axes of the user's eyes. When the position of a target is within the user's field of view (e.g., on a display screen), an instantaneous visual axis of an eye may be determined extending from the known position of the target through the determined center of the iris disc for that eye (i.e., the origin point of the optical axis vector). The instantaneous visual axis will extend within the eye to a point on the eyeball circumference (which point may be considered as consistent with the position of the eye's fovea). Once the instantaneous visual axis 1504 is determined for the user's eye viewing a known target, an offset distance may be calculated that will remain constant to enable determination of successive visual axes for that eye.

Figure 13A:
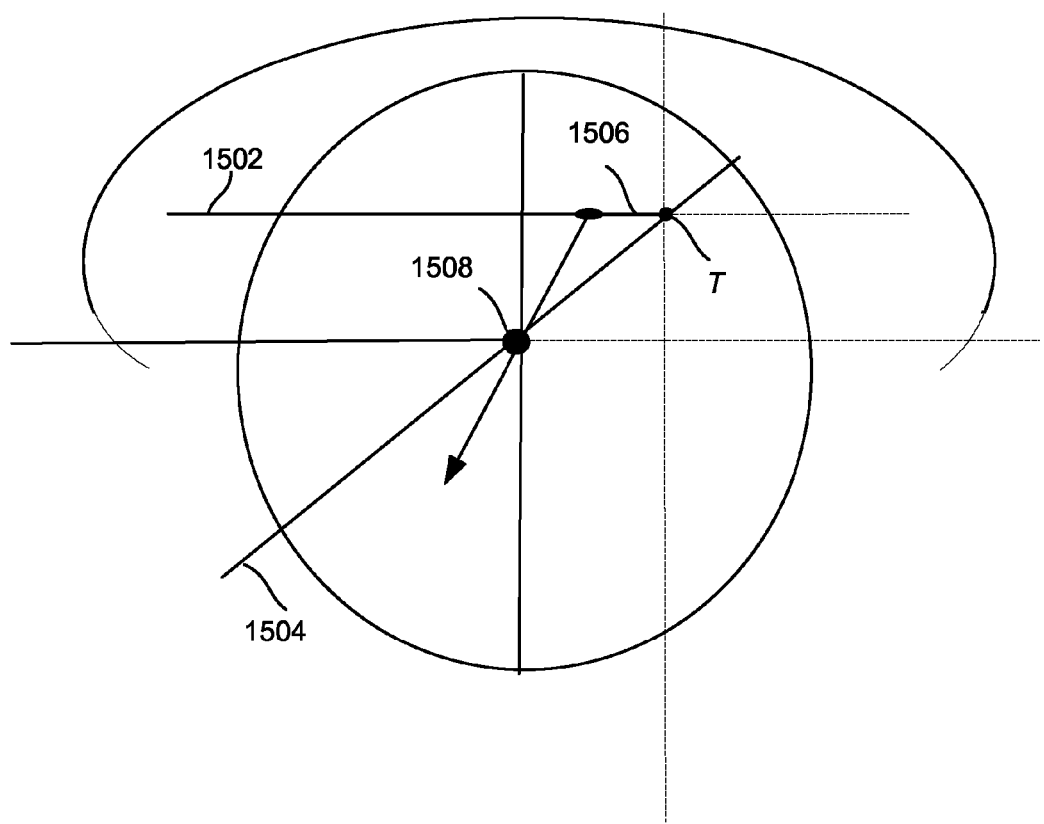
FIGS. 13A and 13B are schematic views of the features of a user's left eye according to an embodiment.
Figure 13B:
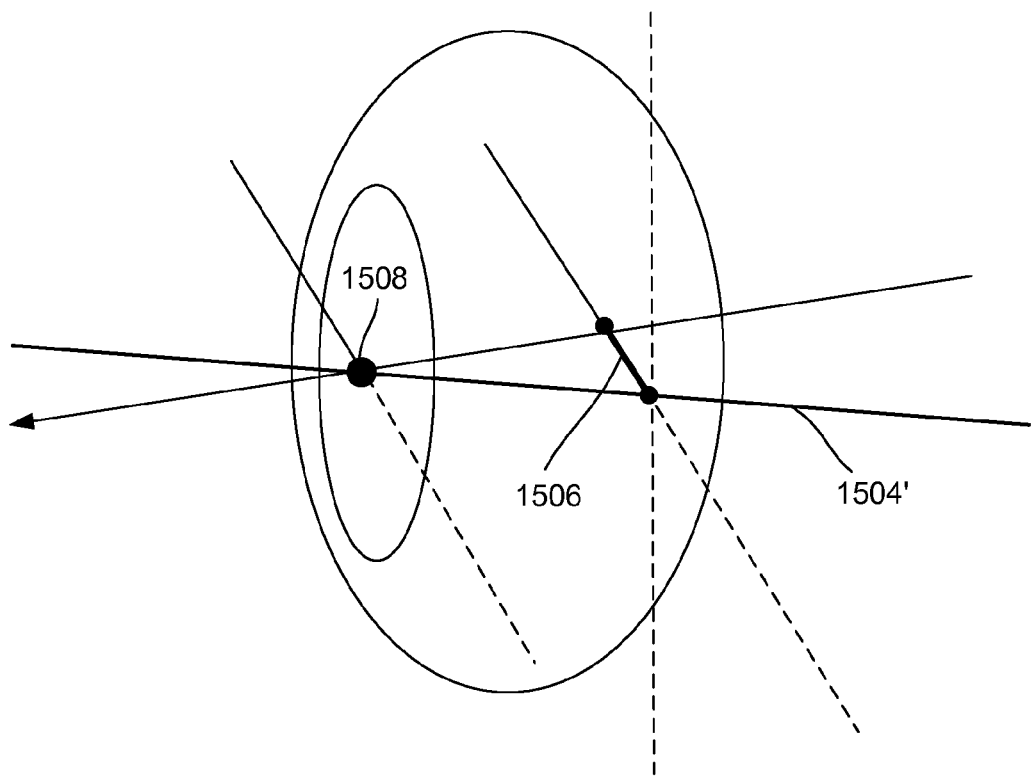

FIG. 13A illustrates an example instantaneous visual axis and other constructed measurements in calculating the offset distance for a user's left eye. A line 1502 constructed between the user's eyeball center points may be extended to intersect the instantaneous visual axis 1504 at or near point T. The offset distance 1506 between the left eyeball center point 70$_{ec}$ and point T, measured along the extended eyeball centers line 1502, remains constant regardless of where the user is looking FIG. 13B illustrates how the user's visual axis may be determined for successive images using the measurements discussed above with respect to FIG. 13A. Thus, for successive images, the user's visual axis for the left eye may be constructed and tracked merely by laterally extending the eyeball centers line 1502 by the known offset distance 1506 from the left eyeball center point, and constructing a visual axis between the new end point and the center of the iris disc of the left eye. In the same manner, an instantaneous visual axis, an offset distance and successive visual axes may be determined for the user's right eye. The user's point-of-gaze for each target viewed may be determined by extending the visual axes for both eyes and determining the point of intersection. This description assumes the model defined by FIG. 6, where all of the user's optical and visual axis vectors lie in the same plane.

In practice, the visual axes, optical axis vectors, eyeball centers, and foveae of a user's eyes will not precisely match the schematic model, nor do all of these features typically lie in the same plane. However, the algorithm may accommodate requisite features calculated for a user's eyes, even when these features do not lie in the same plane, as is typical.

Figure 14A:
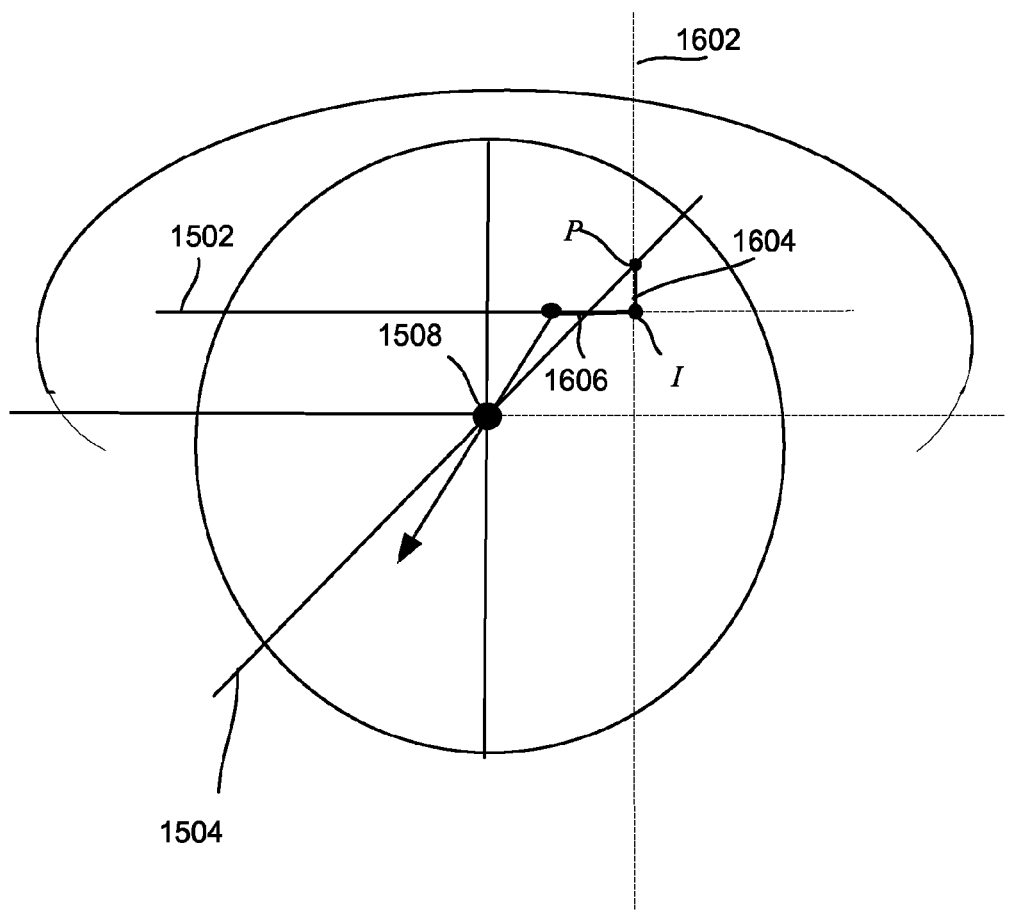
FIGS. 14A and 14B are schematic views of the features of a user's left eye according to an embodiment.

FIG. 14A illustrates a user's left eye in which the fovea is displaced from a local plane. The local plane is defined by three points: the center of the local iris disc (i.e., origin of the optical axis vector) and the two eyeball center points. When features are calculated using images of real eyes, the center of the other iris disc will likely not be in this plane. For this method, two unknowns must be determined in order to track the user's left visual axis: the offset distance from the eyeball center along the eyeball center's extension line, and the offset distance from that endpoint to the visual axis. These distances may be determined by rotating the local plane 90 degrees about the eyeball centers line, giving two mathematically defined planes (i.e., the local plane and a longitudinal plane) at right angles to one another. An instantaneous visual axis may be constructed that extends from the known position of the target being viewed by the user as described above with respect to FIG. 13A.

Figure 14B:
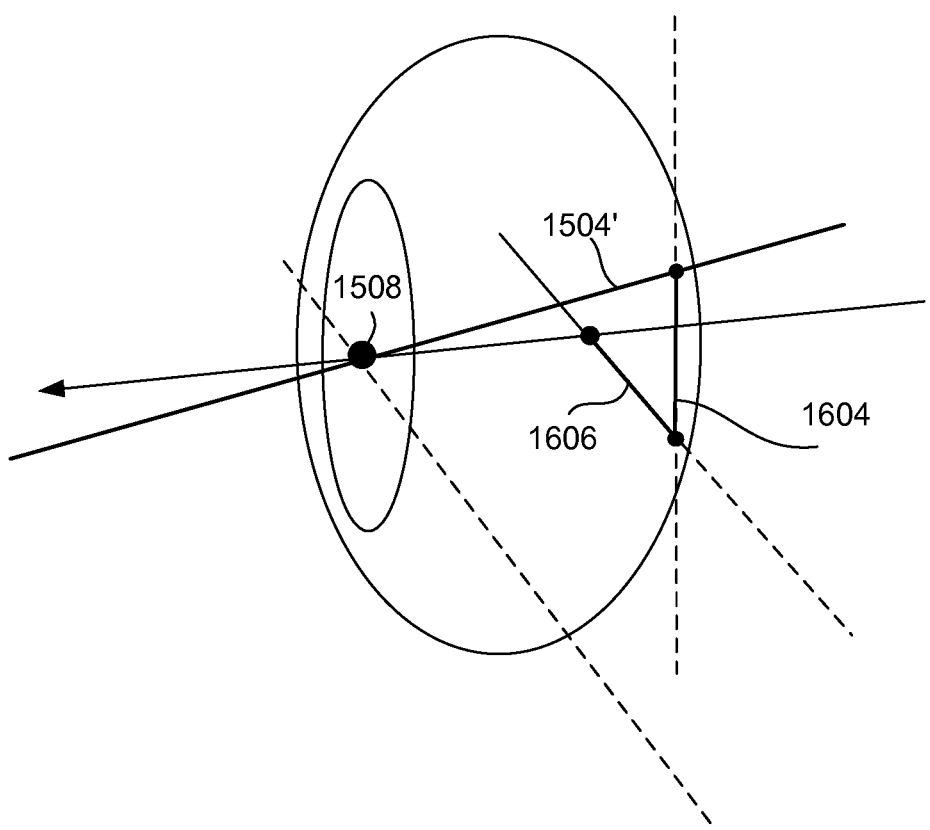

The instantaneous visual axis 1504 intersects the longitudinal plane at a point P. A line 1602 may be constructed within the longitudinal plane that intersects both point P and the eyeball centers extension line at point I. A first offset distance 1606 may be measured from the eyeball center point, along the eyeball center extension line to the intersection point I. A second offset distance 1604 from the point I to point P on the instantaneous visual axis 1504 may be measured. These distances, and the orientation between them will remain constant, wherever the user is looking FIG. 14B illustrates how the user's visual axis may be determined and tracked in successive images using the measurements discussed above with respect to FIG. 14A. The eyeball centers extension line 1502 may be laterally extended by the first offset distance 1606 from the left eyeball center point $70_{ec}$. From the new endpoint (i.e., the ipsilateral endpoint of the eyeball centers extension line 1502), a line that is perpendicular to the eyeball centers extension line may be constructed in the longitudinal plane, extending a length equal to the second offset distance 1604 in the dorsal direction. A visual axis 1504' may be constructed as a line between the endpoint of this perpendicular line and the iris disc center point 1508. Visual axis lines may be similarly determined for the right eye, and both lines may be easily extended outward to indicate the user's point-of-gaze.

In some applications, it may be determined algorithmically that the accuracy of the second offset distance adds no precision. In such cases, successive visual axes may be tracked by the first offset distance only, using only the offset distance from the eyeball center along the eyeball centers extension line, as discussed above with reference to FIGS. 15A and 15B. Further, both methods described are exemplary, and not intended to represent the only possible methods for determining visual axes by using a user's optical axis vectors and eyeball centers. For example, since the visual axis passes through the iris disc center point, the solid angle offset from the optical axis could be determined. For successive images and calculations, this constant solid angle would have to be oriented in space to an existing feature, such as the local plane, for example. The end result would be the same: determination of the visual axis using a user's optical axis vectors and eyeball centers.

Since the same target point is used to determine both visual axes, the axes converge in space at the position of the target point. However, the measured visual axis offsets for any particular target position/user position couplet are not likely to be precisely the same as the offsets measured for any other target point. Therefore, for reasonable accuracy in the completed visual axes measurement result, the visual axes may be determined for several target points at different positions, with the user's head and eyes at different distances from the display upon which the targets are rendered. For example, the user may be asked to sit at points where his or her eyes are approximately 200 mm, 300 mm, and 400 mm from the display screen, while the display presents targets placed at all four corners and the middle of the screen. Images may be captured for each target position couplet while the user is being cued to focus upon the target, and visual axes offsets are calculated for each. The final result may be, for example, the average offset values, the mean values, or some other aggregate value that serves to minimize the visual axes convergence error as seen for all of the target/user position couplets. Further, assuming the user's iris disc diameters are not known, differing iris disc diameter estimates may also be iterated in the same manner.

Several features of a user's eyes that are discussed above may be used in biometric applications, such as identifying a user and verifying his or her identity. Such features include, for example, diameter of each iris, the radius of each of the eyeballs, the distance between the two eyeball center points, and the visual axes offsets. Further, iris grayscale or color contour maps across a single, invariant section through each iris as depicted in an image may also be used to identify one user from a population.

Iris contour maps may be determined from biometric points and features that are discussed above in the various embodiments. These points and features are not visible in images of the user, but may be projected into these images algorithmically to identify points on a user's irises along which the section lines are drawn. Further, these section lines are defined as invariant to the user's point of gaze, orientation of the image sensor, or position/orientation of the user's face within the field of view, always cutting through the same iris topography (image grayscale or color contours) along the section line computed for each image. When coupled with some or all of the other biometric eye measurements listed above, high-confidence iris contour maps may be used to significantly elevate the probability of correct identification of a user. High-confidence iris grayscale contour maps may be obtained if the line drawn through each iris in an image (along which the contour maps are collected) intersects the same points on the irises, regardless of where the user is looking or how his or her head is turned within the 3-axis coordinate system defined by an image sensor's optics.

Figure 15:
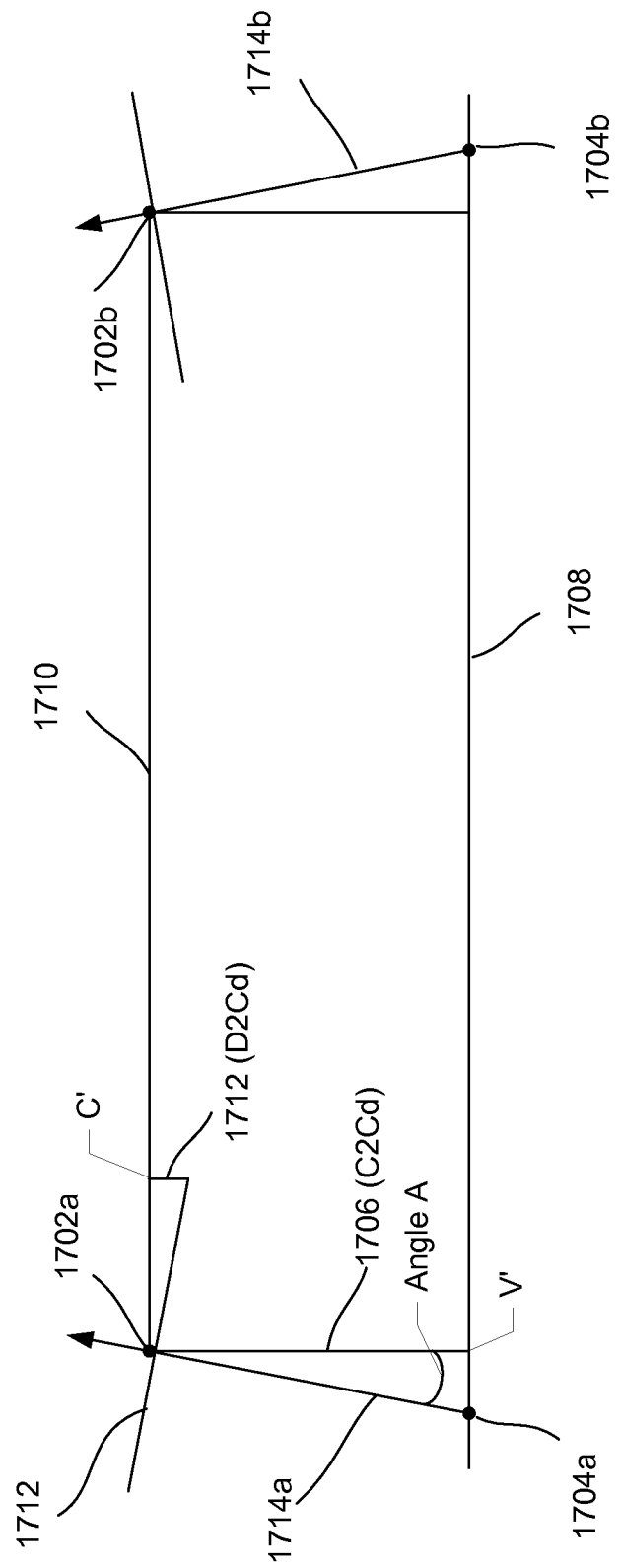
FIG. 15 is a schematic view of a user's eyes positionally related in a 3-axis coordinate system of an image sensor's optic.

FIG. 15 illustrates a user's eyes positionally related as they would be in the 3-axis coordinate system viewed by the image sensor's optics. The user's optical axes "look in" at an angle consistent with a point-of-gaze about 150 mm in front of the user's eyes. The two iris disc center points 1702a, 1702b and the two eyeball center points 1704a, 1704b are shown to be in the same plane. In reality, it is unlikely that all four points calculated for a user will lie exactly in the same plane, but all will be near enough to coplanarity to determine accurate, repeatable iris contour map section lines from one image to the next. The plane sections the iris discs along the same line, regardless of where the user is looking, or how the user's head or eyes are oriented in an image. Since the plane is determined by the four points that define where the user is looking, and the orientation of the user's head and eyes, the plane necessarily sections the iris discs along the same line, regardless of where the user is looking or how the user's head or eyes are oriented in an image.

These section lines may be determined in an image by first measuring distances C2Cd and D2Cd in the 3-axis coordinate system. FIG. 15 illustrates the measurements of these distances for a user's right eye (as seen from below). A line 1706 may be constructed in a local plane defined by the origin of that eye's optical axis vector 1702a and the two eyeball centers 1704a and 1704b. This line 1706 is constructed perpendicular to the eyeball centers line 1708 and passing through the origin of the optical axis vector 1702a. The distance, measured along line 1706, between the eyeball centers line 1708 and the origin of that eye's optical axis vector 1702a is C2Cd. Another line 1712 may be constructed in a different local plane—that defined by the local eyeball center point 1704a and the origin points of the two optical axis vectors 1702a and 1702b. This line 1712 is constructed perpendicular to the iris centers line and passing through the point where the medial half of the iris disc edge intersects this local plane. The distance from the iris centers line 1710 to the iris disc edge intersection point is D2Cd. The angle formed by line 1706 and an eyeball radius line 1714a is substantially identical to the angle formed by line 1712 and a line 1710. Therefore, the sine of that angle multiplied by the iris disc radius (i.e., length of line 1712) also measures D2Cd.

Figure 16:
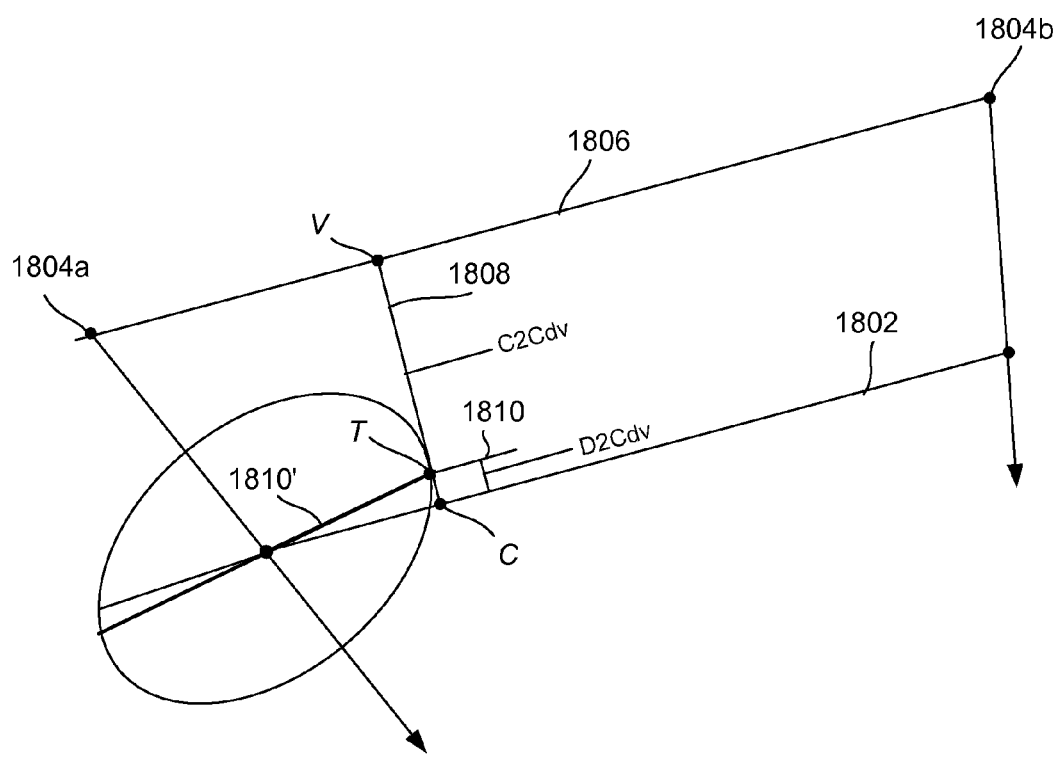
FIG. 16 is a schematic view of a user's right eye orbited in an image.

FIG. 16 illustrates a user's right eye (both spatially and in the image). The iris disc ellipse and the iris center point (all within the image plane) may be determined by the least squares fit, as described above. The iris disc ellipses and center points for the user's eyes may therefore be mapped and constructed within the image, and a line 1802 may be constructed between the two iris center points. Since the eyeball center points 1704a, 1704b of both eyes are known in the 3-axis coordinate system, their counterparts 1804a, 1804b may be identified in the image using the methods described herein, and an imaged eyeball centers line 1806 may be constructed between them. Simple trigonometric functions may be employed to determine the angles $\phi_i$ between the rays from (0,0,0) to 1704a, 1704b and the z-axis. Then a variation of Equation 0 [$h_i$=3726.06 tan $\phi_i$], along with $\theta_i$ values for 1704a, 1704b also computed spatially may be employed to find 1804a, 1804b in the image. A line 1808 in the image may be constructed that is perpendicular to the line 1802 between the imaged iris centers. The line 1808 intersects the imaged iris centers line 1806 at point C, and intersects the imaged eyeball centers line 1802 at point V. The length of line 1808 may be measured as C2Cdv, and:

$$D2Cdv=C2Cdv*D2Cd/C2Cd$$

The lengths C2Cdv and D2Cdv in the image correspond to, and are proportional to, the lengths C2Cd and D2Cd in the 3-axis coordinate system. Another line 1810 that is parallel to line 1802 and offset by a distance of D2Cdv may be constructed in the image. Line 1810 intersects the iris disc at point T, and the iris contour map section line 1810' may be constructed from point T on the ipsilateral iris disc edge, through the iris disc center point, and to the contralateral edge of the iris disc. This process may be duplicated for the left eye within the image.

While the various embodiments are described with reference to determining center point of the user's eyeball, the embodiments may be applied to other subcutaneous anatomical features, such bone structures which, like eyeball centers, are fixed with respect to the user's head and unaffected by gaze angle or facial expressions. The advantages of the various embodiments of the subcutaneous features are not affected by facial expressions or eye movements, and thus may provide a more consistent measurement of the user's head position and orientation that may be possible using only visible facial features.

While the example calculation methods are described herein and in the drawings as being accomplished in a rectilinear three-dimensional coordinate system, the embodiments may also be implemented in a similar manner in other types of three-dimensional coordinate systems including an spherical coordinate systems and an elliptical coordinate system.

Figure 17:
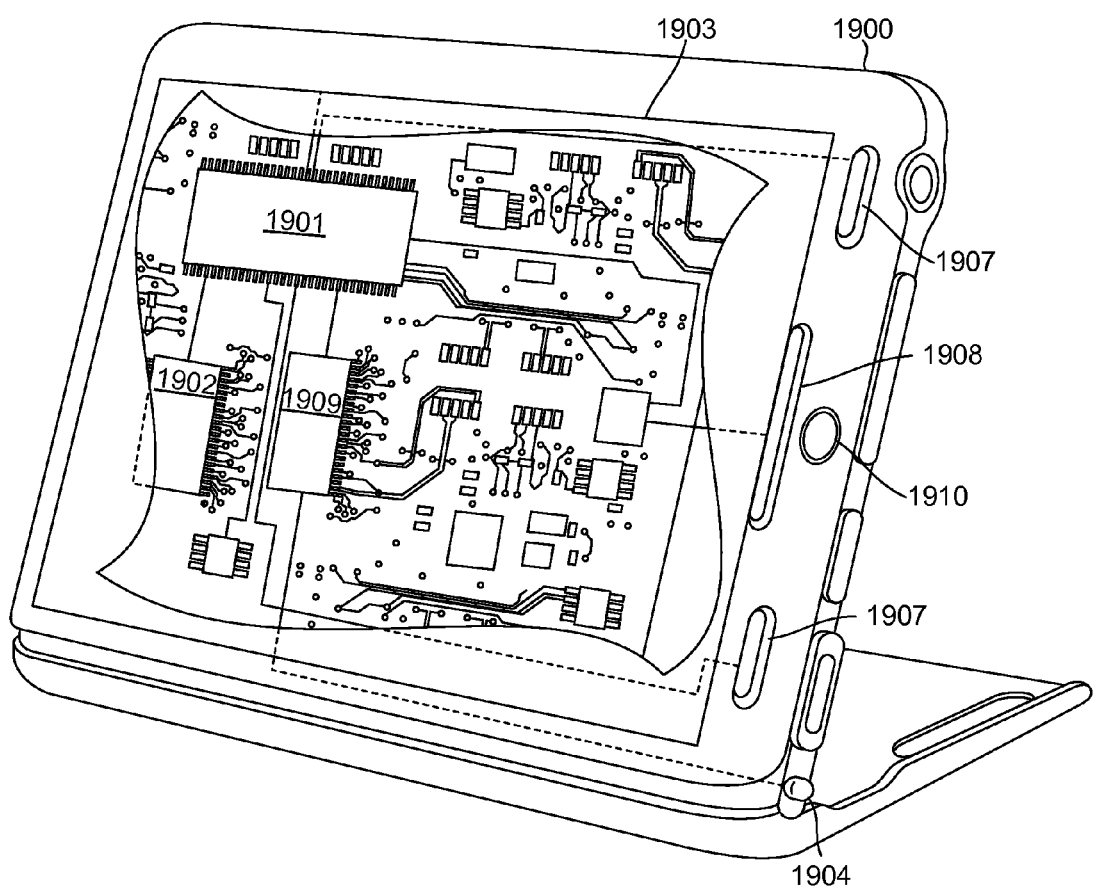
FIG. 17 is a system block diagram of a mobile computing device suitable for use with the embodiments.
Figure 18:
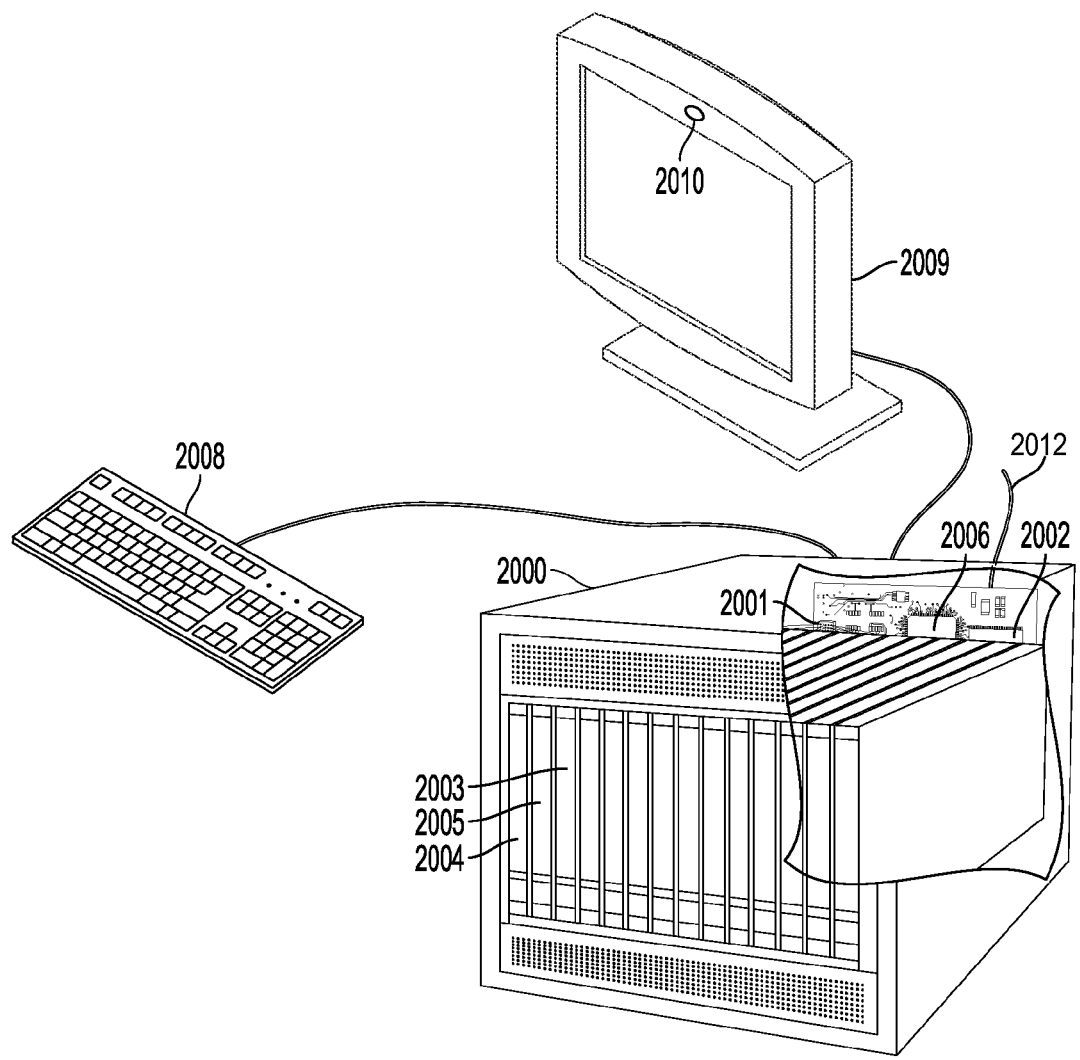
FIG. 18 is a system block of another computing device suitable for use with the embodiments.

The various embodiments may be implemented on a variety of conventional computer systems, such as a mobile device 1900 illustrated in FIG. 17 and a personal computer system 2000 illustrated in FIG. 18.

FIG. 17 shows a mobile device suitable for use with any of the embodiments may include a processor 1901 coupled to a digital camera 1910 capable of imaging a user's face when the device is held in a suitable position. The processor 1901 may also be coupled to internal memory 1902, a display 1903, and other components, such as a speaker 1908. In some implementations, the mobile device 1900 may include an antenna 1904 for sending and receiving electromagnetic radiation that may be connected to a wireless data link and/or cellular telephone transceiver 1905 coupled to the processor 1901. Receiver devices 1900 typically also include menu selection buttons 1907 or rocker switches for receiving user inputs.

Referring to FIG. 18, a computer system 2000 typically includes a processor 2001 coupled to volatile memory 2002 and a large capacity nonvolatile memory, such as a disk drive 2003. The computer system 2000 may include a display 2009 coupled to the processor 2001, as well as a digital camera (e.g., a CCD camera) 2010 positioned to be able to image a user's face. The computer system 2000 may also include a floppy disc drive, compact disc (CD) or DVD disc drive 2004 coupled to the processor 2001.

The computer system 2000 may also include network access ports 2006 coupled to the processor 2001 for establishing data connections with a network 2012, such as a local area network coupled to other broadcast system computers and servers. Computer system 2000 may also include other user interfaces, such as a keyboard 2008.

The processors 1901, 2001 may be any programmable microprocessor, microcomputer or multiple processor chip or chips that may be configured by software instructions (applications) to perform a variety of functions, including the functions of the various embodiments described below. In some mobile receiver devices, multiple processors 2001 may be provided, such as one processor dedicated to wireless communication functions and one processor dedicated to running other applications. Typically, software applications may be stored in the internal memory 1902, 2002, 2003 before they are accessed and loaded into the processor 1901, 2001. The processor 1901, 2001 may include internal memory sufficient to store the application software instructions.

The foregoing method descriptions and the process flow diagrams are provided merely as illustrative examples and are not intended to require or imply that the steps of the various embodiments must be performed in the order presented. As will be appreciated by one of skill in the art, the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

When implemented in software, the functions may be stored as one or more instructions or code on a non-transitory computer-readable or processor-readable storage medium. The steps of a method or algorithm disclosed herein may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

When implemented in hardware, the functionality may be implemented within circuitry of a wireless signal processing circuit that may be suitable for use in a wireless receiver or mobile device. Such a wireless signal processing circuit may include circuits for accomplishing the signal measuring and calculating steps described in the various embodiments.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

Any reference to claim elements in the singular, for example, using the articles "a," "an" or "the" is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for controlling a computing device, comprising:
   obtaining a first digital image of a face of a user of the computing device with a digital camera;
   processing the first digital image to determine a position and orientation of an eyeball of the user beneath a surface of the user's skin by:
      determining an ellipse equation characterizing a first apparent iris disc in a plane of the first digital image by performing a least squares fit of iris-to-sclera boundary pixels in the first digital image; and
      determining a spherical center point location of the eyeball using the determined ellipse equation characterizing the first apparent iris disc in the plane of the first digital image; and
   translating the position determined and the orientation of the user's eyeball into an input command;
   wherein determining the spherical center point location of the eyeball comprises:
      determining coordinates of a center point of an iris disc in a three-dimensional coordinate system based on the determined ellipse equation characterizing the first apparent iris disc;
      calculating a first optical axis vector of the iris disc oriented in the three-dimensional coordinate system based on the center point of the iris disc and on the ellipse equation characterizing the first apparent iris disc;
      projecting the first optical axis vector into the user's eyeball;
      measuring one eyeball radius distance along the projected first optical axis vector from the surface of the iris disc in the user's eyeball;
      storing the projected first optical axis vector;
      calculating at least a second optical axis vector of the iris disc by:
         prompting the user to look in another direction;
         obtaining at a second digital image of the user's face;

determining an ellipse equation characterizing a second apparent iris disc in a plane of the second digital image; and determining three-dimensional coordinates of a second center point of the iris disc based on the determined ellipse equation characterizing the second apparent iris disc;

projecting the at least second optical axis vector into the user's eyeball; and determining an intersection of the projected first and projected at least second optical axis vector.

2. The method of claim 1, further comprising:

repeating operations to determine a center point for both eyeballs; and determining an orientation of the user's head within the digital image based the determined eyeball center points and an inter-eyeball distance between the determined eyeball center points.

3. A computing device, comprising:

a digital camera; and a processor coupled to the camera and configured with processor-executable instructions to perform operations comprising:

obtaining a first digital image of a face of a user of the computing device with the digital camera;

processing the first digital image to determine a position and orientation of an eyeball of the user beneath a surface of the user's skin by:

determining an ellipse equation characterizing a first apparent iris disc in a plane of the first digital image by performing a least squares fit of iris-to-sclera boundary pixels in the first digital image: and determining a spherical center point location of the eyeball using the determined ellipse equation characterizing the first apparent iris disc in the plane of the first digital image; and translating the position determined and the orientation of the user's eyeball into an input command;

wherein determining the spherical center point location of the eyeball comprises:

determining coordinates of a center point of an iris disc in a three-dimensional coordinate system based on the determined ellipse equation characterizing the first apparent iris disc;

calculating a first optical axis vector of the iris disc oriented in the three-dimensional coordinate system based on the center point of the iris disc and on the ellipse equation characterizing the first apparent iris disc;

projecting the first optical axis vector into the user's eyeball;

measuring one eyeball radius distance along the projected first optical axis vector from the surface of the iris disc in the user's eyeball;

storing the projected first optical axis vector;

calculating at least a second optical axis vector of the iris disc by:

prompting the user to look in another direction;

obtaining at a second digital image of the user's face;

determining an ellipse equation characterizing a second apparent iris disc in a plane of the second digital image; and determining three-dimensional coordinates of a second center point of the iris disc based on the determined ellipse equation characterizing the second apparent iris disc;

projecting the at least second optical axis vector into the user's eyeball; and determining an intersection of the projected first and projected at least second optical axis vector.

4. The computing device of claim 3, wherein the processor is configured with processor-executable instructions to perform operations further comprising:

repeating operations to determine a center point for both eyeballs; and determining an orientation of the user's head within the digital image based the determined eyeball center points and an inter-eyeball distance between the determined eyeball center points.

5. A computing device, comprising:

means for obtaining a first digital image of a face of a user of the computing device;

means for processing the first digital image to determine a position and orientation of an eyeball of the user beneath a surface of the user's skin comprising means for determining an ellipse equation characterizing a first apparent iris disc in a plane of the first digital image by performing a least squares fit of iris-to-sclera boundary pixels in the first digital image: and means for determining a spherical center point location of the eyeball using the determined ellipse equation characterizing the first apparent iris disc in the plane of the first digital image; and means for translating the position determined and the orientation of the user's eyeball into an input command;

wherein means for determining the spherical center point location of the eyeball comprises:

means for determining coordinates of a center point of an iris disc in a three-dimensional coordinate system based on the determined ellipse equation characterizing the first apparent iris disc;

means for calculating a first optical axis vector of the iris disc oriented in the three-dimensional coordinate system based on the center point of the iris disc and on the ellipse equation characterizing the first apparent iris disc;

means for projecting the first optical axis vector into the user's eyeball;

means for measuring one eyeball radius distance along the projected first optical axis vector from the surface of the iris disc in the user's eyeball;

means for storing the projected first optical axis vector;

means for calculating at least a second optical axis vector of the iris disc comprising:

means for prompting the user to look in another direction;

means for obtaining at a second digital image of the user's face;

means for determining an ellipse equation characterizing a second apparent iris disc in a plane of the second digital image; and means for determining three-dimensional coordinates of a second center point of the iris disc based on the determined ellipse equation characterizing the second apparent iris disc;

means for projecting the at least second optical axis vector into the user's eyeball; and means for determining an intersection of the projected first and projected at least second optical axis vector.

6. The computing device of claim 5, further comprising:

means for repeating operations to determine a center point for both eyeballs; and means for determining an orientation of the user's head within the digital image based the determined eyeball center points and an inter-eyeball distance between the determined eyeball center points.

7. A non-transitory processor-readable storage medium having stored thereon processor-executable instructions configured to cause a processor of a computing device including a digital camera to perform operations comprising:
obtaining a first digital image of a face of a user of the non-transitory processor readable storage medium with the digital camera;
processing the first digital image to determine a position and orientation of an eyeball of the user a surface of the user's skin by:
determining an ellipse equation characterizing a first apparent iris disc in a plane of the first digital image by performing a least a squares fit of iris-to-sclera boundary pixels in the first digital image; and
determining a spherical center point location of the eyeball using the determined ellipse equation characterizing the first apparent iris disc in the plane of the first digital image; and
translating the position determined and the orientation of the user's eyeball anatomical structure into an input command;
wherein determining the spherical center point location of the eyeball comprises:
determining coordinates of a center point of an iris disc in a three-dimensional coordinate system based on the determined ellipse equation characterizing the first apparent iris disc;
calculating a first optical axis vector of the iris disc oriented in the three-dimensional coordinate system based on the center point of the iris disc and on the ellipse equation characterizing the first apparent iris disc;
projecting the first optical axis vector into the user's eyeball;
measuring one eyeball radius distance along the projected first optical axis vector from the surface of the iris disc in the user's eyeball;
storing the projected first optical axis vector;
calculating at least a second optical axis vector of the iris disc by:
prompting the user to look in another direction;
obtaining at a second digital image of the user's face;
determining an ellipse equation characterizing a second apparent iris disc in a plane of the second digital image; and
determining three-dimensional coordinates of a second center point of the iris disc based on the determined ellipse equation characterizing the second apparent iris disc;
projecting the at least second optical axis vector into the user's eyeball; and
determining an intersection of the projected first and projected at least second optical axis vector.

8. The non-transitory processor-readable storage medium of claim 7, wherein the stored processor-executable instructions are configured to cause the processor to perform operations further comprising:
repeating operations to determine a center point for both eyeballs; and
determining an orientation of the user's head within the digital image based the determined eyeball center points and an inter-eyeball distance between the determined eyeball center points.

9. The method of claim 1, wherein determining the ellipse equation characterizing the first apparent iris disc comprises identifying ellipse defining parameters comprising:
an x-axis offset comprising a x-axis distance to the center of the first apparent iris disc in the first digital image plane;
a y-axis offset comprising a y-axis distance to the center of the first apparent iris disc;
a length of the major axis of an ellipse shape of the first apparent iris disc;
a length of the minor axis of the ellipse shape; and
a rotation angle of the ellipse shape with respect to the x-axis.

10. The method of claim 9, wherein calculating the first optical axis vector of the iris disc oriented in the three-dimensional coordinate system based on the center point of the iris disc and on the ellipse equation characterizing the first apparent iris disc comprises:
identifying (x, y) coordinates of the center point of the first apparent iris disc in the first digital image plane using the x-axis offset and y-axis offset;
calculating (x, y) coordinates of at least two edge points of the first apparent iris disc in the first digital image plane based On the determined ellipse equation characterizing the first apparent iris disc; and
calculating a distance in pixels between an origin point (0,0) in the first digital image plane and each of the at least two edge points of the first apparent iris disc, wherein each of the distances comprises a hypotenuse of a triangle formed by the calculated (x, y) coordinates of the respective edge point.

11. The method of claim 10, wherein calculating the first optical axis vector of the iris disc oriented in the three-dimensional coordinate system based on the center point of the iris disc and on the ellipse equation characterizing the first apparent iris disc further comprises:
calculating lengths of rays from an origin point (0,0,0) in the three-dimensional coordinate system to each of at least two points on a surface of the iris disc in the user's eyeball that correspond to the at least two edge points, wherein the calculations utilize a spatial angle, between each ray and a z-axis, a function relating ray length to the spatial angle and a field of view of the image sensor's optics, and iris radius; and
determining the three-dimensional coordinates of the at least two points on the surface of the iris disc based on the calculated length of the rays.

12. The method of claim 11, wherein calculating the first optical axis vector of the iris disc oriented in the three-dimensional coordinate system based on the center point of the iris disc and on the ellipse equation characterizing the first apparent iris disc further comprises:
determining the three-dimensional coordinates of an iris center point in the user's eyeball based on the determined three-dimensional coordinates of the at least two points on the surface of the iris disc; and
calculating the cross product of a first vector and a second vector, wherein the first vector comprises a vector from the iris center point to one of the at least two points on the surface of the iris disc, and wherein the second vector comprises a vector from the iris center point to another of the at least two points on surface of the iris disc.

13. The computing device of claim 3, wherein the processor is configured with processor-executable instructions to perform operations such that determining the ellipse equation characterizing the first apparent iris disc comprises identifying ellipse defining parameters comprising;

an x-axis offset comprising a x-axis distance to the center of the first apparent iris disc in the first digital image plane;
a y-axis offset comprising a y-axis distance to the center of the first apparent iris disc;
a length of the major axis of an ellipse shape of the first apparent iris disc;
a length of the minor axis of the ellipse shape; and
a rotation angle of the ellipse shape with respect to the x-axis.

14. The computing device of claim 13, wherein the processor is configured with processor-executable instructions to perform operations such that calculating the first optical axis vector of the iris disc oriented in the three-dimensional coordinate system based on the center point of the iris disc and on the ellipse equation characterizing the first apparent iris disc comprises:
identifying (x, y) coordinates of the center point of the first apparent iris disc in the first digital image plane using the x-axis offset and y-axis offset;
calculating (x, y) coordinates of at least two edge points of the first apparent iris disc in the first digital image plane based on the determined ellipse equation characterizing the first apparent iris disc; and
calculating a distance in pixels between an origin point (0,0) in the first digital image plane and each of the at least two edge points of the first apparent iris disc, wherein each of the distances comprises a hypotenuse of a triangle formed by the calculated (x, y) coordinates of the respective edge point.

15. The computing device of claim 14, wherein the processor is configured with processor-executable instructions to perform operations such that calculating the first optical axis vector of the iris disc oriented in the three-dimensional coordinate system based on the center point of the iris disc and on the ellipse equation characterizing the first apparent iris disc further comprises:
calculating lengths of rays from an origin point (0,0,0) in the three-dimensional coordinate system to each of at least two points on a surface of the iris disc in the user's eyeball that correspond to the at least two edge points, wherein the calculations utilize a spatial angle between each ray and a z-axis, a function relating ray length to the spatial angle and a field of view of the image sensor's optics, and iris radius; and
determining the three-dimensional coordinates of the at least two points on the surface of the iris disc based on the calculated length of the rays.

16. The computing device of claim 15, wherein the processor is configured with processor-executable instructions to perform operations such that calculating the first optical axis vector of the iris disc oriented in the three-dimensional coordinate system based on the center point of the iris disc and on the ellipse equation characterizing the first apparent iris disc further comprises:
determining the three-dimensional coordinates of an iris center point in the user's eyeball based on the determined three-dimensional coordinates of the at least two points on the surface of the iris disc; and
calculating the cross product of a first vector and a second vector, wherein the first vector comprises a vector from the iris center point to one of the at least two points on the surface of the iris disc, and wherein the second vector comprises a vector from the iris center point to another of the at least two points on surface of the iris disc.

17. The computing device of claim 5, wherein means for determining the ellipse equation characterizing the first apparent iris disc comprises means for identifying ellipse defining parameters comprising:
an x-axis offset comprising a x-axis distance to the center of the first apparent iris disc in the first digital image plane;
a y-axis offset comprising a y-axis distance to the center of the first apparent iris disc;
a length of the major axis of an ellipse shape of the first apparent iris disc;
a length of the minor axis of the ellipse shape; and
a rotation angle of the ellipse shape with respect to the x-axis.

18. The computing device of claim 17, wherein means for calculating the first optical axis vector of the iris disc oriented in the thee-dimensional coordinate system based on the center point of the iris disc and on the ellipse equation characterizing the first apparent iris disc comprises:
means for identifying (x, y) coordinates of the center point of the first apparent iris disc in the first digital image plane using the x-axis offset and y-axis offset;
means for calculating (x, y) coordinates of at least two edge points of the first apparent iris disc in the first digital image plane based on the determined ellipse equation characterizing the first apparent iris disc; and
means for calculating a distance in pixels between an origin point (0,0) in the first digital image plane and each of the at least two edge points of the first apparent iris disc, wherein each of the distances comprises a hypotenuse of a triangle formed by the calculated (x, y) coordinates of the respective edge point.

19. The computing device of claim 18, wherein means for calculating the first optical axis vector of the iris disc oriented in the thee-dimensional coordinate system based on the center point of the iris disc and on the ellipse equation characterizing the first apparent iris disc further comprises:
means for calculating lengths of rays from an origin point (0,0,0) in the three-dimensional coordinate system to each of at least two points on a surface of the iris disc in the user's eyeball that correspond to the at least two edge points, wherein the means for calculating utilize a spatial angle between each ray and a z-axis, a function relating ray length to the spatial angle and a field of view of the image sensor's optics, and iris radius; and
means for determining the three-dimensional coordinates of the at least two points on the surface of the iris disc based on the calculated length of the rays.

20. The computing device of claim 19, wherein means for calculating the first optical axis vector of the iris disc oriented in the three-dimensional coordinate system based on the center point of the iris disc and on the ellipse equation characterizing the first apparent iris disc further comprises:
means for determining the three-dimensional coordinates of an iris center point in the user's eyeball based on the determined three-dimensional coordinates of the at least two points on the surface of the iris disc; and
means for calculating the cross product of a first vector and a second vector, wherein the first vector comprises a vector from the iris center point to one of the at least two points on the surface of the iris disc, and wherein the second vector comprises a vector from the iris center point to another of the at least two points on surface of the iris disc.

21. The non-transitory processor-readable storage medium of claim 7, wherein the stored processor-executable instructions are configured to cause the processor to perform operations such that determining the ellipse equation characterizing the first apparent iris disc comprises identifying ellipse defining parameters comprising:
- an x-axis offset comprising a x-axis distance to the center of the first apparent iris disc in the first digital image plane;
- a y-axis offset comprising a y-axis distance to the center of the first apparent iris disc;
- a length of the major axis of an ellipse shape of the first apparent iris disc;
- a length of the minor axis of the ellipse shape; and
- a rotation angle of the ellipse shape with respect to the x-axis.

22. The non-transitory processor-readable storage medium of claim 21, wherein the stored processor-executable instructions are configured to cause the processor to perform operations such that calculating the first optical axis vector of the iris disc oriented in the three-dimensional coordinate system based on the center point of the iris disc and on the ellipse equation characterizing the first apparent iris disc comprises:
- identifying (x, y) coordinates of the center point of the first apparent iris disc in the first digital image plane using the x-axis offset and y-axis offset;
- calculating (x, y) coordinates of at least two edge points of the first apparent iris disc in the first digital image plane based on the determined ellipse equation characterizing the first apparent iris disc; and
- calculating a distance in pixels between an origin point (0,0) in the first digital image plane and each of the at least two edge points of the first apparent iris disc, wherein each of the distances comprises a hypotenuse of a triangle formed by the calculated (x, y) coordinates of the respective edge point.

23. The non-transitory processor-readable storage medium of claim 22, wherein the stored processor-executable instructions are configured to cause the processor to perform operations such that calculating the first optical axis vector of the iris disc oriented in the three-dimensional coordinate system based on the center point of the iris disc and on the ellipse equation characterizing the first apparent iris disc further comprises:
- calculating lengths of rays from an origin point (0,0,0) in the three-dimensional coordinate system to each of at least two points on a surface of the iris disc in the user's eyeball that correspond to the at least two edge points, wherein the calculations utilize a spatial angle between each ray and a z-axis, a function relating ray length to the spatial angle and a field of view of the image sensor's optics, and iris radius; and
- determining the three-dimensional coordinates of the at least two points on the surface of the iris disc based on the calculated length of the rays.

24. The non-transitory processor-readable storage medium of claim 23, wherein the stored processor-executable instructions are configured to cause the processor to perform operations such that calculating the first optical axis vector of the iris disc oriented in the three-dimensional coordinate system based on the center point of the iris disc and on the ellipse equation characterizing the first apparent iris disc further comprises:
- determining the three-dimensional coordinates of an iris center point in the user's eyeball based on the determined three-dimensional coordinates of the at least two points on the surface of the iris disc; and
- calculating the cross product of a first vector and a second vector, wherein the first vector comprises a vector from the iris center point to one of the at least two points on the surface of the iris disc, and wherein the second vector comprises a vector from the iris center point to another of the at least two points on surface of the iris disc.

* * * * *